US008163552B2

(12) United States Patent
Vollmers et al.

(10) Patent No.: US 8,163,552 B2
(45) Date of Patent: Apr. 24, 2012

(54) ADENOCARCINOMA SPECIFIC ANTIBODY SAM-6, AND USES THEREOF

(75) Inventors: Heinz Vollmers, Wurzburg (DE); Hans-Konrad Müller-Hermelink, Wurzburg (DE)

(73) Assignee: Patrys Limited (AU)

( * ) Notice: Subject to any disclaimer, the term of this patent is extended or adjusted under 35 U.S.C. 154(b) by 0 days.

(21) Appl. No.: 10/579,290

(22) PCT Filed: Nov. 12, 2004

(86) PCT No.: PCT/EP2004/012970
§ 371 (c)(1),
(2), (4) Date: May 15, 2006

(87) PCT Pub. No.: WO2005/047332
PCT Pub. Date: May 26, 2005

(65) Prior Publication Data
US 2008/0108133 A1   May 8, 2008

(30) Foreign Application Priority Data

Nov. 14, 2003   (EP) .................................... 03026161

(51) Int. Cl.
C07K 16/18   (2006.01)
C12N 15/00   (2006.01)
C12N 15/11   (2006.01)
(52) U.S. Cl. ..................................... 435/330; 530/387.7
(58) Field of Classification Search ................. 435/330; 530/387.7
See application file for complete search history.

(56) References Cited

U.S. PATENT DOCUMENTS

| | | | | |
|---|---|---|---|---|
| 5,610,280 | A | 3/1997 | Brandt et al. | 530/387.5 |
| 5,639,641 | A | 6/1997 | Pedersen et al. | |
| 5,639,863 | A | 6/1997 | Dan | 530/388.8 |
| 5,763,224 | A | 6/1998 | Caras et al. | 435/69.6 |
| 6,210,670 | B1 * | 4/2001 | Berg | 424/153.1 |
| 6,677,442 | B1 | 1/2004 | Wang et al. | 536/23.2 |
| 6,995,240 | B1 | 2/2006 | Panayi et al. | 530/350 |
| 7,049,132 | B1 | 5/2006 | Lee | 435/320.1 |
| 7,468,183 | B2 | 12/2008 | Nilsson et al. | |
| 7,521,046 | B2 | 4/2009 | Nilsson et al. | |
| 7,785,589 | B2 | 8/2010 | Nilsson et al. | |
| 2004/0048243 | A1 | 3/2004 | Arap et al. | 435/5 |
| 2005/0123571 | A1 | 6/2005 | Rossini et al. | 424/277.1 |
| 2005/0191294 | A1 | 9/2005 | Arap et al. | 424/143.1 |
| 2006/0239968 | A1 | 10/2006 | Arap et al. | 424/93.2 |
| 2008/0003200 | A1 | 1/2008 | Arap et al. | 424/85.2 |

FOREIGN PATENT DOCUMENTS

| | | |
|---|---|---|
| EP | 0 502 812 A1 | 9/1992 |
| EP | 09098786 | 4/1997 |
| EP | 1 106 183 A2 | 6/2001 |
| WO | 92/16624 | 10/1992 |
| WO | 96/16990 | 6/1996 |
| WO | 97/02479 | 1/1997 |
| WO | 97/13844 A1 | 4/1997 |
| WO | 99/28461 | 6/1999 |
| WO | 99/53051 | 10/1999 |
| WO | 99/65935 A2 | 12/1999 |
| WO | 00/012562 | 3/2000 |
| WO | 00/37489 A2 | 6/2000 |
| WO | WO 00/56772 A1 | 9/2000 |
| WO | 01/62932 A1 | 8/2001 |
| WO | 02/02641 A1 | 1/2002 |
| WO | 02/12502 A2 | 2/2002 |
| WO | 02/084277 A1 | 10/2002 |
| WO | 03/011907 A3 | 2/2003 |
| WO | WO 03/048321 A2 | 6/2003 |
| WO | 03/076472 A2 | 9/2003 |
| WO | 03/076472 A3 | 9/2003 |
| WO | WO 03/084477 A2 | 10/2003 |
| WO | 2004/005351 A2 | 1/2004 |
| WO | 2004/020999 A1 | 3/2004 |
| WO | 2004/003019 * | 6/2004 |
| WO | 2004/081027 A2 | 9/2004 |
| WO | 2004/081027 A3 | 9/2004 |
| WO | 2005/001052 A2 | 1/2005 |
| WO | 2005/045428 A2 | 5/2005 |
| WO | 2005/047332 A1 | 5/2005 |
| WO | 2005/049635 A2 | 6/2005 |
| WO | 2005/049635 A3 | 6/2005 |
| WO | 2005/065418 A2 | 7/2005 |
| WO | 2005/085862 A1 | 9/2005 |
| WO | 2005/092922 A2 | 10/2005 |
| WO | 2005/092922 A3 | 10/2005 |
| WO | 2005/094159 A2 | 10/2005 |
| WO | WO 2010/088739 A1 | 8/2010 |

OTHER PUBLICATIONS

Rauschert et al (Lab. Invest. 88:375-386 (2008)).*
MacCallum et al. (J. Mol. Biol. 262:732-745 (1996)).*
de Pascalis et al. (Journal of Immunology 169, 3076-3084 (2002)).*
Casset et al. (BBRC 307, 198-205, (2003)).*
Vajdos et al. (J. Mol. Biol. 320, 415-428 (2002)).*
Holm et al (Mol. Immunol. 44: 1075-1084 (2007)).*
Chen et al. (J. Mol. Bio. 293, 865-881 (1999)).*
Wu et al. (J. Mol. Biol. 294, 151-162 (1999)).*
Brummell et al. (Biochemistry 32:1180-1187 (1993)).*
Kobayashi et al. (Protein Engineering 12:879-844 (1999)).* Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Boder et al. (Proc. Nat'l Acad. Sci. USA 97:10701 (2000)).*
Kipriyanov et al. (Protein Engineering 10:445 (1997)).*
Holmes et al. (J. Immunol. 167:296 (2001)).*
Wilson et al. (J. Exp. Med. 187:59 (1998)).*
Lantto and Ohlin (J. Biol. Chem. 277:45108 (2002)).*
Dufner (Trends Biotechnol. 24(11):523-29 (2006)).*
Bost et al. (Immunol. Invest. (1988) 17:577-586).*
Bendayan (J. Histochem. Cytochem. (1995) 43:881-886).*

(Continued)

*Primary Examiner* — Lynn Bristol

(74) *Attorney, Agent, or Firm* — Pillsbury Winthrop Shaw Pittman LLP

(57) ABSTRACT

A purified polypeptide that binds to neoplastic cells, which may be an antibody, is produced by the hybridoma SAM-6, a method for its production and use in the treatment and diagnosis of neoplasms.

23 Claims, 14 Drawing Sheets

OTHER PUBLICATIONS

Ward et al. (Nature 341:544-546 (1989)).*
Lederman et al (Molecular Immunology 28:1171-1181, 1991)).*
Li et al (Proc. Natl. Acad. Sci. USA 77:3211-3214, 1980)).*
Rudikoff et al (Proc Natl Acad Sci USA 1982 vol. 79 p. 1979).*
Berger, C.L., et al., A Lymphocyte Cell Surface Heat Shock Protein Homologous to the Endoplasmic Reticulum Chaperone, Immunoglobulin Heavy Chain Binding Protein BIP, Int. J. Cancer, 71:1077-1085 (1997).
Bjorge et al., Complement-Regulatory Proteins in Ovarian Malignancies, Int. J. Cancer, 70:14-25 (1997).
Brandlein et al., "Natural IgM Antibodies and Immunosurveillance Mechanisms Against Epithelial Cancer Cells in Humans," Cancer Research, 63: 7995-8005, Nov. 15, 2003.
Brändlein et al., Characterization of Five New Fully Human Monoclonal IgM Antibodies Isolated from Carcinoma Patients, Proceedings of the Annual Meeting of the American Association for Cancer Research 43:970, Mar. 2002 (Abstract).
Brändlein et al., Human Monoclonal IgM Antibodies with Apoptotic Activity isolated from Cancer Patients, Human Antibodies 11:107-119, 2002.
Brändlein, S., et al., CFR-1 Receptor as Target for Tumor-specific Apoptosis Induced by the Natural Human Monoclonal Antibody PAM-1, Oncology Reports, 11:777-784 (2004).
Brändlein, S., et al., Cysteine-rich Fibroblast Growth Factor Receptor 1, a New Marker for Precancerous Epithelial Lesions Defined by the Human Monoclonal Antibody PAM-1, Cancer Research, 63:2052-2061 (2003).
Brändlein, S., et al., PAM-1, a Natural Human IgM Antibody as New Tool for Detection of Breast and Prostate Precursors, Human Antibodies, 13:97-104 (2004).
Chen, G., et al., Protein Profiles Associated With Survival in Lung Adenocarcinoma, www.pnas.orq/cgi/doi/10.1073/pnas.2233850100 pp. 1-6 (2003).
Database entry AAB02178 dated Jun. 11, 1996.
Faller et al., HAB-1, a New Heteromyeloma for Continuous Production of Human Monoclonal Antibodies, Br. J. Cancer 62:595-598 (1990).
Gonatas et al., MG-160, A Membrane Sialoglycoprotein of the Medial Cisternae of the Rat Golgi Apparatus, Binds Basic Fibroblast Growth Factor and Exhibits a High level of Sequence Identity to a Chicken Fibroblast Growth Factor Receptor, J. Cell Science 108:457-467, 1995.
Grossman, H.B., Natural Antibody to a Human Bladder Carcinoma Cell Line, Cancer Immunol. Immunother. 13:89-92 (1982).
Hensel et al., A New Variant of Cystein-Rich FGF Receptor (CFR-1) Specifically Expressed on Tumor Cells, Proceedings of the American Association for Cancer Research 41:698 (abstract 4438), Mar. 2000.
Hensel et al., A Novel Proliferation-associated Variant of CFR-1 Defined by a Human Monoclonal Antibody, Laboratory Investigation 81:1097-1108, 2001.
Hensel et al., Characterization of Glycosylphosphatidylinositol-linked Molecule CD55/Decay-accelerating Factor as the Receptor for Antibody SC-1-induced Apoptosis, Cancer Research 59:5299-5306, 1999.
Hensel et al., Mitogenic Autoantibodies in Helicobacter pylori-Associated Stomach Cancerogenesis, International Journal of Cancer 81:229-235, 1999.
Hensel, F., et al., "Regulation of the new coexpressed CD55 (decay-accelerating factor) receptor on stomach carcinoma cells involved in antibody SC-1-induced apoptosis", Laboratory Investigation, 81(11):1553-1563 (2001).
Huang et al., Sulindac Sulfide-induced Apoptosis Involves Death Receptor 5 and the Caspase 8-dependent Pathway in Human Colon and Prostate Cancer Cells, Cancer Research 61:6918-6924 (2001).
Iwadate, Y., et al., Molecular Classification and Survival Prediction in Human Gliomas Based on Proteome Analysis, Cancer Research, 64:2496-2501 (2004).
Jamora, C., et al., Inhibition of Tumor Progression by Suppression of Stress Protein GRP78/BiP Induction in Fibrosarcoma B/C10ME, Proc. Natl. Acad. Sci. USA, 93:7690-7694 (1996).
Jansson, et al., The Human Repertoire of Antibody Specificities Against Thomsen-Friedenreich and TN-carcinoma-associated antigens as defined by Monoclonal Antibodies, Cancer Immunology 34:294-298, 1992.
Kamitani, H., et al., Expression of 15-Lipoxygenase by Human Colerectal Carcinoma Caco-2 Cells During Apoptosis and Cell Differentiation, The Journal of Biological Chemistry, 273(34):21569-21577 (1998).
Lee, A.S., Mammalian Stress Response: Induction of the Glucose-Regulated Protein Family, Current Opinion in Cell Biology, 4:267-273 (1992).
Little, E., et al., The Glucose-Regulated Proteins (GRP78 and GRP94): Functions, Gene Regulation, and Applications, Critical Reviews in Eukaryonic Gene Expression, 4(1):1-18 (1994).
Liu et al., Towards Proteome-Wide Production of Monoclonal Antibody by Phage Display, J. Mol. Bio. 315:1063-1073 (2002).
Mammalian Gene Collection (MGC) Program Team, "Generation and Initial Analysis of more than 15,000 Full-Length Human and Mouse cDNA Sequences" PNAS USA 99:16,899-16,903 (2002).
Mintz, P.J., et al., Fingerprinting the Circulating Repertoire of Antibodies from Cancer Patients, Nature Biotechnology, 21:57-63 (2003).
Misra, U.K., et al., The Role of Grp 78 in $\alpha_2$-Macroglubulin-Induced Signal Transduction, The Journal of Biological Chemistry, 277(44):42082-42087 (2002).
Mourelatos et al., Cloning and Sequence Analysis of the Human MG160, a Fibroblast Growth Factor and E-Selectin Binding Membrane Sialoglycoprotein of the Golgi Apparatus, DNA Cell Biol. 12:1121-1128 (1996).
Myung, J-K, et al., Expressional Patterns of Chaperones in Ten Human Tumor Cell Lines, Proteome Science, 2:8:1-21 (2004).
Pfaff, M., et al., Human Monoclonal Antibody Against a Tissue Polypeptide Antigen-related Protein from a Patient with a Signet-Ring Cell Carcinoma of the Stomach, Cancer Research, 50:5192-5198 (1990).
Pohle et al., Lipoptosis: Tumor Specific Cell Death by Antibody-Induced Intracellular Lipid Accumulation, Cancer Research, 64:11, 3900-3906 (2004).
Sato, K., et al., Immunotherapy Using Heat-Shock Protein Preparations of Leukemia Cells After Syngenic Bone Marrow Transplantation in Mice, Blood, 98(6):1852-1857 (2001).
Sugawara, S., et al., Suppression of Stress Protein GRP78 Induction in Tumor B/C10ME Eliminates Resistance to Cell Mediated Cytotoxicity, Cancer Research, 53:6001-6005 (1993).
Vollmers et al., "Apoptosis of Stomach Carcinoma Cells Induced by a Human Monoclonal Antibody," Cancer 76:550-558 (1995).
Vollmers et al., "Human Monoclonal Antibodies from Stomach Carcinoma Patients React with Helicobacter pylori and Stimulate Stomach Cells in vitro," Cancer 74:1525-1532, 1994.
Vollmers et al., "SC-1, a Functional Human Monoclonal Antibody against Autologous Stomach Carcinoma Cells," Cancer Res. 49:2471-2476, 1989.
Vollmers et al., Adjuvant Therapy for Gastric Adenocarcinoma with the Apoptosis-Inducing Human Monoclonal Antibody SC-1: First Clinical and Histopathological Results, Oncology Reports 5:549-552 (1998).
Vollmers, H.P., et al., Monoclonal Antibodies NORM-1 and NORM-2 Induce More Normal Behavior of Tumor Cells In Vitro and Reduce Tumor Growth In Vivo, Cell, 40:547-557 (1985).
Vollmers, P., et al., Tumor-Specific Apoptosis Induced by the Human Monoclonal Antibody SC-1: A New Therapeutical Approach for Stomach Cancer, Oncology Reports, 5:35-40 (1998).
Wixler et al., "Identification of Novel Interaction Partners for the conserved membrane proximal region of alpha-integrin cytoplasmic domains," FEBS Letters vol. 445, Feb. 26, 1999.
Timmermann W., et al.,"Immunotherapy: an Antibody Against Stomach Cancer" Blick Jan. 1999, Artikel 6, internet page http://www.uni-wuerzburg.de/blick1999-1/991do6-t.html.

Arap, M.A., et al., Cell Surface Expression of the Stress Response Chaperone GRP78 Enables Tumor Targeting by Circulating Ligands, *Cancer Cell*, 2004, 6:275-284.

Ilag, L.I., Power, B., Udabage, L., U.S. Appl. No. 61/151,149, "SAM-6 Variants, Target and Methods of Use", Feb. 9, 2009.

Vollmers, H.P., U.S. Appl. No. 11/945,916, "Novel Glycosylated Peptide Target in Neoplastic Cells", Nov. 27, 2007.

Vollmers, P., U.S. Appl. No. 10/578,856, "Human Monoclonal Antibody Having Fat-Reducing Effect", Jul. 18, 2006.

U.S. Appl. No. 12/702,974, filed Feb. 2010, Ilag.

\* cited by examiner

A

B

A

B

SEQUENCE LISTING

<160> NUMBER OF SEQ ID NOS: 4

<210> SEQ ID NO 1

-continued

```
<211> LENGTH: 96
<212> TYPE: PRT
<213> ORGANISM: Homo sapiens
<220> FEATURE:
<221> NAME/KEY: misc_feature
<223> OTHER INFORMATION: variable region of the light chain (VL) of
      antibody SAM-6

<400> SEQUENCE: 1

Ser Tyr Val Leu Thr Gln Pro Pro Ser Val Ser Val Ser Pro Gly
 1               5                  10                  15

Gln Thr Ala Ser Ile Thr Cys Ser Gly Asp Lys Leu Gly Asp Lys
                20                  25                  30

Tyr Ala Cys Trp Tyr Gln Gln Lys Pro Gly Gln Ser Pro Val Leu
                35                  40                  45

Val Ile Tyr Gln Asp Ser Lys Arg Pro Ser Gly Ile Pro Glu Arg
                50                  55                  60

Phe Ser Gly Ser Asn Ser Gly Asn Thr Ala Thr Leu Thr Ile Ser
                65                  70                  75

Gly Thr Gln Ala Met Asp Glu Ala Asp Tyr Tyr Cys Gln Ala Trp
                80                  85                  90

Asp Ser Ser Ile Val Val
                95

<210> SEQ ID NO 2
<211> LENGTH: 288
<212> TYPE: DNA
<213> ORGANISM: Homo sapiens
<220> FEATURE:
<221> NAME/KEY: misc_feature
<223> OTHER INFORMATION: variable region of the light chain (VL) of
      antibody SAM-6

<400> SEQUENCE: 2 tcc tat gtg ctg act cag cca ccc tca gtg tcc gtg tcc cca gga       45
Ser Tyr Val Leu Thr Gln Pro Pro Ser Val Ser Val Ser Pro Gly
 1               5                  10                  15 cag aca gcc agc atc acc tgc tct gga gat aaa ttg ggg gat aaa       90
Gln Thr Ala Ser Ile Thr Cys Ser Gly Asp Lys Leu Gly Asp Lys
                20                  25                  30 tat gct tgc tgg tat cag cag aag cca ggc cag tcc cct gtg ctg      135
Tyr Ala Cys Trp Tyr Gln Gln Lys Pro Gly Gln Ser Pro Val Leu
                35                  40                  45 gtc atc tat caa gat agc aag cgg ccc tca ggg atc cct gag cga      180
Val Ile Tyr Gln Asp Ser Lys Arg Pro Ser Gly Ile Pro Glu Arg
                50                  55                  60 ttc tct ggc tcc aac tct ggg aac aca gcc act ctg acc atc agc      225
Phe Ser Gly Ser Asn Ser Gly Asn Thr Ala Thr Leu Thr Ile Ser
                65                  70                  75 ggg acc cag gct atg gat gag gct gac tat tac tgt cag gcg tgg      270
Gly Thr Gln Ala Met Asp Glu Ala Asp Tyr Tyr Cys Gln Ala Trp
                80                  85                  90 gac agc agc att gtg gta                                          288
Asp Ser Ser Ile Val Val
                95

<210> SEQ ID NO 3
<211> LENGTH: 110
<212> TYPE: PRT
<213> ORGANISM: Homo sapiens
<220> FEATURE:
<221> NAME/KEY: misc_feature
<223> OTHER INFORMATION: variable region of the heavy chain (VH) of
      antibody SAM-6
```

```
<400> SEQUENCE: 3

Gln Val Gln Leu Val Glu Ser Gly Gly Gly Val Val Gln Pro Gly
  1               5                  10                  15

Arg Ser Leu Arg Leu Ser Cys Ala Ala Ser Gly Phe Thr Phe Ser
             20                  25                  30

Ser Tyr Ala Met His Trp Val Arg Gln Ala Pro Gly Lys Gly Leu
             35                  40                  45

Glu Trp Val Ala Val Ile Ser Tyr Asp Gly Ser Asn Lys Tyr Tyr
             50                  55                  60

Ala Asp Ser Val Lys Gly Arg Phe Thr Ile Ser Arg Asp Asn Ser
             65                  70                  75

Lys Asn Thr Leu Tyr Leu Gln Met Asn Ser Leu Arg Ala Glu Asp
             80                  85                  90

Thr Ala Val Tyr Tyr Cys Ala Arg Asp Arg Leu Ala Val Ala Gly
             95                 100                 105

Arg Pro Phe Asp Tyr
            110

<210> SEQ ID NO 4
<211> LENGTH: 330
<212> TYPE: DNA
<213> ORGANISM: Homo sapiens
<220> FEATURE:
<221> NAME/KEY: misc_feature
<223> OTHER INFORMATION: variable region of the heavy chain (VH) of
      antibody SAM-6

<400> SEQUENCE: 4 cag gtg cag ctg gtg gag tct ggg gga ggc gtg gtc cag cct ggg      45
Gln Val Gln Leu Val Glu Ser Gly Gly Gly Val Val Gln Pro Gly
  1               5                  10                  15 agg tcc ctg aga ctc tcc tgt gca gcc tct gga ttc acc ttc agt      90
Arg Ser Leu Arg Leu Ser Cys Ala Ala Ser Gly Phe Thr Phe Ser
             20                  25                  30 agc tat gct atg cac tgg gtc cgc cag gct cca ggc aag ggg ctg     135
Ser Tyr Ala Met His Trp Val Arg Gln Ala Pro Gly Lys Gly Leu
             35                  40                  45 gag tgg gtg gca gtt ata tca tat gat gga agc aat aaa tac tac     180
Glu Trp Val Ala Val Ile Ser Tyr Asp Gly Ser Asn Lys Tyr Tyr
             50                  55                  60 gca gac tcc gtg aag ggc cga ttc acc atc tcc aga gac aat tcc     225
Ala Asp Ser Val Lys Gly Arg Phe Thr Ile Ser Arg Asp Asn Ser
             65                  70                  75 aag aac acg ctg tat ctg caa atg aac agc ctg aga gct gag gac     270
Lys Asn Thr Leu Tyr Leu Gln Met Asn Ser Leu Arg Ala Glu Asp
             80                  85                  90 acg gct gtg tat tac tgt gcg aga gat cgg tta gca gtg gct ggt     315
Thr Ala Val Tyr Tyr Cys Ala Arg Asp Arg Leu Ala Val Ala Gly
             95                 100                 105 aga cct ttt gac tac                                             330
Arg Pro Phe Asp Tyr
            110
```

US 8,163,552 B2

ADENOCARCINOMA SPECIFIC ANTIBODY SAM-6, AND USES THEREOF

This application is a U.S. National phase of PCT application no. PCT/EP/2004/012970, filed Nov. 12, 2004, and claims priority to European patent application no. 030206161.4, filed Nov. 14, 2003.

BACKGROUND OF THE INVENTION

The present invention is related to the field of cancer diagnosis and treatment and, more specifically, to the identification of polypeptides, such as antibodies, useful in the diagnosis, detection, monitoring, and treatment of neoplasms in a mammal, e.g., a human.

Although recent advances in the medical field have significantly improved the rate of survival among cancer patients, a large number of cancer-related deaths still could be prevented by the early diagnosis of the tumor. Accordingly, at the time of initial diagnosis, an alarming number of patients have already reached late stages of the disease.

Approximately 75% of women are diagnosed with ovarian cancer after the disease has already reached an advanced stage (stage III or IV) because the symptoms of ovarian cancer are often vague or "silent." Despite aggressive surgical intervention and new chemotherapeutic regimens, the overall 5-year survival rate for these women with advanced stage ovarian cancer has remained constant over the past 30 years, at approximately 15%. Conversely, women diagnosed with cancer confined to the ovary (stage 1) have an overall 5-year survival rate approaching 90%.

Clearly, there is a need for the early and improved detection and treatment of neoplasms (e.g. adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, lobular carcinoma of the of the breast, ductal carcinoma of the breast, adenocarcinoma of the pancreas, adenocarcinoma of the ovary, or adenocarcinoma of the uterus) as this would increase the chance of treating the neoplasm and, thereby, lead to an improved prognosis for long-term survival.

SUMMARY OF THE INVENTION

We have discovered a polypeptide named SAM-6 which reacts with an epitope specific for neoplastic cells. This polypeptide is not only an excellent diagnostic tool, but also can inhibit cell proliferation, induce the intracellular accumulation of lipids and apoptosis of the neoplastic cells to which it binds. These characteristic result in a treatment for neoplastic diseases that lacks the side-effects of many existing therapeutics.

The present invention features polypeptides, such as monoclonal antibodies that may be used in the diagnosis and treatment of a neoplasm. Accordingly in the first aspect the invention features a purified polypeptide that binds to neoplastic cells, wherein said polypeptide has an amino acid sequence substantially identical to the sequence of SEQ ID NO 1 and SEQ ID NO 3, and wherein said polypeptide specifically binds to BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196), and LOU-NH91 (DSMZ Accession No. ACC 393) cells and not to non-neoplastic cells.

In a second aspect, the invention features a purified polypeptide that binds to neoplastic cells, wherein said polypeptide has an amino acid sequence substantially identical to the sequence of SEQ ID NO 1 and SEQ ID NO 3, and wherein said polypeptide specifically binds to BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196) and LOU-NH91 (DSMZ Accession No. ACC 393) cells and not to non-neoplastic cells, and wherein said neoplastic cell is a adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, adenocarcinoma of the esophagus lobular carcinoma of the breast, ductal carcinoma of the breast, adenocarcinoma of the pancreas, adenocarcinoma of the ovary, and adenocarcinoma of the uterus cell.

In the third aspect, the invention features a purified polypeptide that binds to neoplastic cells, wherein said polypeptide has an amino acid sequence substantially identical to the sequence of SEQ ID NO 1 and SEQ ID NO 3, and wherein said polypeptide specifically binds to a adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, lobular carcinoma of the breast, ductal carcinoma of the breast, adenocarcinoma of the pancreas, adenocarcinoma of the ovary, and adenocarcinoma of the uterus cell and not to a non-neoplastic cell.

In a desirable embodiment of the first three aspects of the invention, the polypeptide inhibits cell proliferation when bound to a neoplastic cell, but does not inhibit cell proliferation of a non-neoplastic cell.

In a second desirable embodiment of the first three aspects of the invention, the polypeptide binds to low density lipoproteins (LDL) and/or oxidized low density lipoproteins (ox-LDL) and/or binds to very low density lipoproteins (VLDL) and induces the intracellular accumulation of lipids when bound to a neoplastic cell, but does not induce the intracellular accumulation of lipids in a non-neoplastic cell.

In a third desirable embodiment of the first three aspects of the invention, the polypeptide induces apoptosis of a neoplastic cell to which it binds, but does not induce apoptosis of a non-neoplastic cell.

In a forth desirable embodiments of the first three aspects of the invention, the polypeptide includes an antibody or a functional fragment thereof. For example, the functional fragment may be selected from the group consisting of $V_L$, $V_H$, $F_V$, $F_C$, Fab, Fab', and $F(ab')_2$. In addition, the functional fragment may include a fragment that is substantially identical to the sequence of SEQ ID NOS: 1 and/or 3, or may include a fragment of the sequence of SEQ ID NOS: 1 and/or 3.

In a fifth desirable embodiment of the first three aspects of the invention the complementarity-determining regions (CDRs) of the polypeptides nucleic acid sequence comprises a nucleic acid sequences that are substantially identical to nucleotides 67-99 (CDR1), 145-165 (CDR2) and 262-288 (CDR3) of SEQ ID NO 2 of the variable region of the light chain ($V_L$). While the complementarity-determining regions (CDRs) of the polypeptides nucleic acid sequence comprises a nucleic acid sequences that are substantially identical to nucleotides 91-105 (CDR1), 148-198 (CDR2) and 295-330 (CDR3) of SEQ ID NO 4 of the variable region of the heavy chain ($V_H$).

The fourth aspect of the invention features a purified polypeptide that includes the amino acid sequence of SEQ ID NO 1; or the amino acid sequence of SEQ ID NO:3.

In the fifth aspect, the invention features a purified polypeptide that includes the amino acid sequence of SEQ ID NOS:1 and 3.

In a first embodiment of the first five aspects of the invention the complementarity-determining regions (CDRs) of the polypeptides sequence comprises a amino acid sequences that are substantially identical to the amino acid sequences Ser-Gly-Asp-Lys-Leu-Gly-Asp-Lys-Tyr-Ala-Cys (CDR1), Gln-Asp-Ser-Lys-Arg-Pro-Ser (CDR2) and Gln-Ala-Trp-Asp-Ser-Ser-Ile-Val-Val (CDR3) of SEQ ID NO 1 of the variable region of the light chain ($V_L$). While the complementarity determining regions (CDRs) of the polypeptides amino acid sequence comprises a amino acid sequences that are substantially identical to amino acid sequence Ser-Tyr-Ala-Met-His (CDR1), Val-Ile-Ser-Tyr-Asp-Gly-Ser-Asn-Lys-Tyr-Tyr-Ala-Asp-Ser-Val-Lys-Gly (CDR2) and Asp-Arg-Leu-Ala-Val-Ala-Gly-Arg-Pro-Phe-Asp-Tyr (CDR3) of SEQ ID No 3 of the variable region of the heavy chain ($V_H$).

In a second desirable embodiment of the first five aspects of the invention, the polypeptide is an antibody, such as a monoclonal antibody, e.g., a human monoclonal antibody.

In the sixth aspect, the invention features a cell that expresses the polypeptide of the first aspect; in the eighth aspect, the invention features a cell that expresses the polypeptide of the second aspect; and in the ninth aspect, the invention features a cell that expresses the polypeptide of the third aspect.

In the seventh aspect the invention features a cell that expresses a polypeptide that comprises a sequence that is substantially identical to the amino acid sequence of SEQ ID NO:1.

In the eight aspect the invention features a cell that expresses a polypeptide that comprises a sequence that is substantially identical to the amino acid sequence of SEQ ID NO:3.

In the ninth aspect, the invention features a cell that expresses a polypeptide that includes a sequence that is substantially identical to the amino acid sequence of SEQ ID NO:1 or 3, and in desirable embodiments of this aspect, the polypeptide includes the sequence of SEQ ID NO:1 or 3, or both SEQ ID NO:1 and 3.

In the tenth aspect, the invention features a method of generating the cell according of the sixth aspect. This method involves the steps of: (a) contacting lymphocytes with a heteromyeloma cell line under conditions that result in the fusion of a lymphocyte with a heteromyeloma cell, where the fusion results in a hybridoma, (b) determining whether said hybridoma produces a polypeptide that inhibits proliferation in a neoplastic cell to which it binds, but does not inhibit proliferation in a non-neoplastic cell and, (c) determining whether the hybridoma produces a polypeptide that specifically binds to at least one of BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196) and LOU-NH91 (DSMZ Accession No. ACC 393) cells and not to non-neoplastic cells.

In the eleventh aspect, the invention features a method of generating the cell of the seventh aspect. This method involves the steps of: (a) contacting lymphocytes with a heteromyeloma cell line under conditions; that result in the fusion of a lymphocyte with a heteromyeloma cell, where the fusion results in a hybridoma, (b) determining whether said hybridoma produces a polypeptide that induces intracellular accumulation of lipids in a neoplastic cell to which it binds, but does not induce intracellular accumulation of lipids in a non-neoplastic cell and (c) determining whether the hybridoma produces a polypeptide that specifically binds to at least one of BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196) and LOU-NH91 (DSMZ Accession No. ACC 393) cells and not to non-neoplastic cells.

In the twelfth aspect, the invention features a method of generating the cell of the ninth aspect. This method involves the steps of: (a) contacting lymphocytes with a heteromyeloma cell line under conditions that result in the fusion of a lymphocyte with a heteromyeloma cell, where the fusion results in a hybridoma, (b) determining whether said hybridoma produces a polypeptide that induces apoptosis of a neoplastic cell to which it binds, but does not induce apoptosis of a non-neoplastic cell, and (c) determining whether the hybridoma produces a polypeptide that specifically binds to at least one of BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196) and LOU-NH91 (DSMZ Accession No. ACC 393) cells and not to non-neoplastic cells.

In a thirteenth aspect, the invention features a use of the purified polypeptide of any one of the first five aspects of the invention in a method of diagnosing a neoplasm in a mammal, e.g., a human. This method involves the steps of: (a) contacting a cell or tissue sample of the mammal with the purified polypeptide of any one of the first thirteen aspects of the invention, and (b) detecting whether the purified polypeptide binds to the cell or tissue sample, where binding of the purified polypeptide to the cell or tissue sample is indicative of the mammal having a neoplasm.

In desirable embodiments of the thirteenth aspect of the invention, the neoplasm is a adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, lobular carcinoma of the breast, ductal carcinoma of the breast, adenocarcinoma of the pancreas, adenocarcinoma of the ovary, or adenocarcinoma of the uterus. In further desirable embodiments of this aspect, the polypeptide is an antibody or the polypeptide is conjugated to a detectable agent selected from the group consisting of a radionuclide, a fluorescent marker, an enzyme, a cytotoxin, a cytokine, and a growth inhibitor. Further, the polypeptide may be conjugated to a protein purification tag, e.g., a cleavable protein purification tag.

In the fourteenth aspect, the invention features a use of the purified polypeptide of any one of the first five aspects of the invention in a method of treating a proliferative disorder in a mammal, e.g., a human. This method involves the step of contacting a cell sample with the purified polypeptide of any one of the first seven aspects, where binding of the purified polypeptide to the cell results in the reduction in proliferation of the cell.

In desirable embodiments of the fourteenth aspect of the invention, the proliferative disorder is a adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, lobular carcinoma of the breast, ductal carcinoma of the breast, adenocarcinoma of the pancreas, adenocarcinoma of the ovary, and adenocarcinoma of the uterus. In further desirable embodiments of this aspect, the polypeptide is an antibody or the polypeptide is conjugated to a detectable agent selected from the group consisting of a radionuclide, a fluorescent marker, an enzyme, a cytotoxin, a cytokine, and a growth inhibitor. Desirably, the detectable agent is capable of inducing apoptosis of the cell. In addition, the polypeptide may be conjugated to a protein purification tag, e.g., a protein purification tag that is cleavable.

In the fifteenth aspect, the invention features a use of the purified polypeptide of any one of the first five aspects of the invention in a method of treating a proliferative disorder in a mammal, e.g., a human. This method involves the step of contacting a cell with the purified polypeptide of any one of the first seven aspects of the invention, where binding of the purified polypeptide to the cell results in the intracellular accumulation of lipids in said cell.

In desirable embodiments of the sixteenth aspect of the invention, the proliferative disorder is a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, and adenocarcinoma of the uterus. In further desirable embodiments of this aspect, the polypeptide is an antibody or the polypeptide is conjugated to a detectable agent selected from the group consisting of a radionuclide, a fluorescent marker, an enzyme, a cytotoxin, a cytokine, and a growth inhibitor. Desirably, the detectable agent is capable of inhibiting cell proliferation of the cell. In addition, the polypeptide may be conjugated to a protein purification tag, e.g., a protein purification tag that is cleavable.

In the seventeenth aspect, the invention features a use of the purified polypeptide of any one of the first five aspects of the invention in a method of treating a proliferative disorder in a mammal, e.g., a human. This method involves the step of contacting a cell with the purified polypeptide of any one of the first seven aspects of the invention, where binding of the purified polypeptide to the cell results in the induction of apoptosis of said cell.

In desirable embodiments of the eighteenth aspect of the invention, the proliferative disorder is a stomach adenocarcinoma, colorectal adenocarcinoma, squamous cell lung carcinoma, lung adenocarcinoma, squamous cell carcinoma of the esophagus, adenocarcinoma of the pancreas, urothel carcinoma of the urinary bladder, renal cell carcinoma of the kidney, adenocarcinoma of the prostate, ductal carcinoma of the breast, lobular carcinoma of the breast, adenocarcinoma of the ovary, adenocarcinoma of the endometrium, and adenocarcinoma of the uterus. In further desirable embodiments of this aspect, the polypeptide is an antibody or the polypeptide is conjugated to a detectable agent selected from the group consisting of a radionuclide, a fluorescent marker, an enzyme, a cytotoxin, a cytokine, and a growth inhibitor. Desirably, the detectable agent is capable of inhibiting cell proliferation of the cell. In addition, the polypeptide may be conjugated to a protein purification tag, e.g., a protein purification tag that is cleavable.

In a nineteenth aspect the invention features the treatment of neoplastic cells in the human body with a medicament that contains the purified polypeptide of any one of the first five aspects of the invention in a pharmaceutically acceptable carrier for the production of a medicament that inhibits cell proliferation.

In a twentieth aspect the invention features the treatment of neoplastic cells in the human body with a medicament that contains the purified polypeptide of any one of the first five aspects of the invention in a pharmaceutically acceptable carrier for the production of a medicament that induces intracellular accumulation of lipids.

In a twenty-first aspect the invention features the treatment of neoplastic cells in the human body with a medicament that contains the purified polypeptide of any one of the first five aspects of the invention in a pharmaceutically acceptable carrier for the production of a medicament that induces apotose.

In the twenty-second aspect the invention features the treatment of neoplastic cells in the human body with a medicament that contains the purified polypeptide of any one of the first five aspects of the invention in a pharmaceutically acceptable carrier for the production of a medicament that inhibits all proliferation and induces the intracellular accumulation of lipids and induces apoptosis.

In the twenty-third aspect, the invention features a diagnostic agent that contains the purified polypeptide of any one of the first five aspects of the invention.

The twenty-fourth aspect of the invention features an isolated nucleic acid molecule that contains the sequence of SEQ ID NO:2 or SEQ ID NO:4.

In the twenty-fifth aspect, the invention features a vector, for instance, a plasmid or viral expression vector, containing the nucleic acid molecule of the twenty-forth aspect. Furthermore, the vector may be contained in a cell, such as a mammalian, e.g., a human, cell.

DEFINITIONS

By "detectable agent" is meant a compound that is linked to a diagnostic agent to facilitate detection. Such a "detectable agent" may be covalently or non-covalently linked to a diagnostic agent. In addition, the linkage may be direct or indirect. Examples of "detectable agents" include, protein purification tags, cytotoxins, enzymes, paramagnetic labels, enzyme substrates, co-factors, enzymatic inhibitors, dyes, radionuclides, chemiluminescent labels, fluorescent markers, growth inhibitors, cytokines, antibodies, and biotin.

By a "diagnostic agent" is meant a compound that may be used to detect a neoplastic cell by employing any one of the assays described herein as well as any other method that is standard in the art. A diagnostic agent may include, for example, an antibody which specifically binds to at least one of the following cells: BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196) or LOU-NH91 (DSMZ Accession No. ACC 393) but not to non-neoplastic cells. In addition, a "diagnostic agent" may inhibit cell proliferation, induce apoptosis, or both only when it is bound to a neoplastic cell, but not a non-neoplastic cell.

Examples of neoplastic cells that may be detected with such a "diagnostic agent" include adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, lobular carcinoma of the breast, ductal carcinoma of the breast, adenocarcinoma of the pancreas, adenocarcinoma of the ovary, or adenocarcinoma of the uterus. Moreover, a "diagnostic agent" may include, for example, peptides, polypeptides, synthetic organic molecules, naturally-occurring organic molecules, nucleic acid molecules, and components thereof, as well as one or more detectable agent covalently or non-covalently linked to the diagnostic agent.

By a "functional fragment," as used herein in reference to polypeptide, is meant a fragment that retains at least one biological activity of the full-length polypeptide. Examples of such a biological activity are the ability to specifically bind an antigen, induce apoptosis, and/or inhibit cell proliferation. These biological activities may be determined, for example, using any one of the assays described herein.

Examples of functional fragments of an antibody are $V_L$, $V_H$, $F_V$, $F_C$, Fab, Fab', or F(ab')$_2$ fragments (see, e.g., Huston et al., Cell Biophys. 22:189-224, 1993; and Harlow and Lane, Antibodies: A Laboratory Manual, Cold Spring Harbor Laboratory, 1988). Desirably, a "functional fragment" has an amino acid sequence that is substantially identical to a fragment, e.g., 5, 10, 15, 20, 15, 30, 50, 75, or 100 contiguous amino acids, of the amino acid sequence of SEQ ID NO:1 or 3. In more desirable embodiments, a "functional fragment" is identical to a fragment of the sequence of SEQ ID NO: 1 or 3. Such a "functional fragment" may contain 5, 10, 15, 20, 15, 30, 50, 75, or 100 contiguous amino acids of SEQ ID NO: 1 or 3, or may be the entire amino acid sequence of SEQ ID NO: 1 or 3.

By "complementarity-determining regions", as used herein, the immunoglobulin's hypervariable segments are meant. This term considers that $V_L$, and $V_H$ regions are not uniformly variable; rather most of their amino acid variations are concentrated into three short hypervariable sequences, which are essential for the specificity of the antibody. The identification of the CDRs was supported by BLAST-Software (Altschul, Stephen F., Thomas L. Madden, Alejandro A. Schäffer, Jinghui Zhang, Zheng Zhang, Webb Miller, and David J. Lipman (1997), "Grapped BLAST and PSI-BLAST: a new generation of protein database search programs", Nucleic Acids Res. 25:3389-3402. (NCBI database)).

A "hybridoma," as used herein, is any cell that is artificially created by the fusion of a normal cell such as an activated lymphocyte with a neoplastic cell, e.g., a myeloma. The hybrid cell, which results from the fusion of at least two cells, may produce a monoclonal antibody or T cell product identical to those produced by the immunologically-competent parent. In addition, these cells, like the neoplastic parent, are immortal.

"Inhibiting cell proliferation," as used herein, refers to a reduction in the rate of cell division of a cell in comparison with the normal rate of cell division of that type of cell. Inhibition of cell proliferation may be assayed using a number of methods standard in the art, for example, the MTT cell proliferation assay described herein, BrdU incorporation, and $^3$H thymidine uptake. Such assays are described, for example, in Ausubel et al., *Current Protocols in Molecular Biology*, Wiley Interscience, New York, 2001; and Sambrook et al., *Molecular Cloning: A Laboratory Manual*, Cold Spring Harbor Laboratory, N.Y., 1989. Desirably, the inhibition of cell proliferation is 20%, 40%, 50%, or 75%. In desirable embodiments, the inhibition of cell proliferation is 80%, 90%, 95%, or even a complete inhibition of cell proliferation.

"Binding of lipids" as used herein means any interaction between lipids, especially low density lipoproteins (LDL) and/or ox LDL and the polypeptide, which is strong enough to interfere with the cell cycle of a neoplastic cell. The interference finally leads to the intracellular accumulation of lipids. Yet it is unclear whether the polypeptide interacts with the lipids first to form a complex that is subsequently interacting with the neoplastic cell or whether the polypeptide interacts directly with a receptor on the surface of neoplastic cells.

The polypeptide, which is an antibody, may be active in its monomeric or in its pentameric form.

"Intracellular accumulation of lipids" as referred to herein means increasing concentration of intracellular lipids, especially of low density lipoproteins (LDL) and/or ox LDL, in comparison to the normal concentration of lipids in that type of cell. LDL was shown to be the intracellularly enriched lipid form by a chromatographic analysis documenting that Cholesterolester and Triglycerids where increased in cells incubated with the purified polypeptide. It is only LDL that contains both forms in these amounts. In the consequence the intracellular lipid accumulation leads to apoptosis, e.g. "Lipoptosis", of neoplastic cells.

Intracellular lipid accumulation may be assayed and visualized using a number of methods standard in the art for example Sudan III staining of neutral lipids described herein or staining with the fluorescence stain Nile Red (Greenspan, P., Mayer, E. P., and Fowler, D. Nile Red: A Selective Fluorescent Stain for Intracellular Lipid Droplets. J. Cell Biol. 100, 965-973, 1985).

"Inducing apoptosis," as used herein, refers to the appearance of characteristics in a cell that are well defined in the art (see, e.g., Wyllie et al., Br. J. Cancer 80 Suppl. 1:34-37, 1999; Kerr et al., Br. J. Cancer 26:239-257, 1972). These characteristics include morphological characteristics, such as membrane blebbing, DNA condensation, as well as changes in F-actin content, mitochondrial mass, and membrane potential. The induction of apoptosis may be assayed using a number of methods standard in the art, for example, a cell death ELISA, TUNEL staining, DNA stains, e.g., Hoechst 33258, and staining with various vital dyes such as acridine orange, Mito Tracker Red® staining (Molecular Probes, Eugene, Oreg.), and Annexin V® staining (Becton Dickinson, N.J.). As used herein "inducing apoptosis" refers to an increase in the number of cells undergoing apoptosis when compared with a control cell population. For instance, the increase of apoptosis may be 10%, 20%, 40%, 50%, or 75%. In desirable embodiments, the induction of apoptosis results in an increase of apoptosis that is 2-fold, 3-fold, 10-fold, or even 100-fold over that seen in a control cell population.

A "neoplastic cell," as used herein, refers to a cell which is undergoing cell division, not undergoing apoptosis, or both, under inappropriate conditions. For example, a "neoplastic cell" may undergo cell division when a corresponding non-neoplastic cell does not undergo cell division, or, alternatively, a "neoplastic cell" may not respond to normal cell-cycle checkpoint controls.

A "proliferative disease," as used herein, refers to any disorder that results in the abnormal proliferation of a cell. Specific examples of proliferative diseases are various types of neoplasms, such as adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, lobular carcinoma of the breast, ductal carcinoma of the breast, adenocarcinoma of the pancreas, adenocarcinoma of the ovary, or adenocarcinoma of the uterus. However, proliferative diseases may also be the result of the cell becoming infected with a transforming virus.

A "protein purification tag," as used herein, is a peptide, e.g., an epitope tag, that is covalently or non-covalently added to a protein to aid in the purification of the protein. Desirably such peptides bind with high affinity to an antibody or to another peptide such as biotin or avidin. Commercially available examples of epitope tags include His-tags, HA-tags, FLAG®-tags, and c-Myc-tags. However, any epitope that is recognized by an antibody also may be used as a protein purification tag. See, for example, Ausubel et al., *Current*

Protocols in Molecular Biology, Wiley Interscience, New York, 2001; and Sambrook et al., Molecular Cloning: A Laboratory Manual, Cold Spring Harbor Laboratory, N.Y., (1989). Protein purification tags may be cleaved from a protein, for example, by using an enzyme, e.g., thrombin, or a chemical, e.g., cyanogen bromide.

By "specifically recognize," as used herein in reference to a polypeptide, e.g., an antibody, is meant an increased affinity of a polypeptide for a particular protein, e.g., an antigen, relative to an equal amount of any other protein. For example, an antibody, e.g., the SAM-6 human monoclonal antibody, that specifically binds to BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196) or LOU-NH91 (DSMZ Accession No. ACC 393), or BXPC-3 (ATCC Accession No. CRL-1687) cells desirably has an affinity for its antigen that is least 2-fold, 5-fold, 10-fold, 30-fold, or 100-fold greater than for an equal amount of any other antigen, including related antigens. Binding of a polypeptide to another polypeptide may be determined as described herein, and by any number of standard methods in the art, e.g., Western analysis, ELISA, or co-immunoprecipitation.

By "substantially identical" is meant a polypeptide or nucleic acid exhibiting at least 75%, 80%, 85%, or 90% identity to a reference amino acid (e.g., the sequence of SEQ ID NO:1 or 3 or nucleic acid sequence (e.g., the sequence of SEQ ID NO:2 or 4. In desirable embodiments, the polypeptide or nucleic acid sequence is at least 95%, 98%, 99%, or 100% identical to a reference amino acid or nucleic acid sequence. For polypeptides, the length of comparison sequences will generally be at least 5, 10, or 15 amino acids and desirably at least 20 or 25 contiguous amino acids. In more desirable embodiments, the length of comparison sequences is at least 30, 50, 75, 90, 95, or 100 contiguous amino acids, or even the full-length amino acid sequence. For nucleic acids, the length of comparison sequences will generally be at least 15, 30, or 45 contiguous nucleotides, and desirably at least 60 contiguous nucleotides. In more desirable embodiments, the length of comparison sequences is at least 75, 150, 225, 270, 285, or 300 contiguous nucleotides, or even the full-length nucleotide sequence.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705).

Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blossom." In addition, the multiple alignment parameters may include an open gap penalty of 10.0, an extend gap penalty of 0.1, as well as setting the similarity matrix to "blossom," the delay divergent to 40%, and the gap distance to 8.

By "purified" or "isolated" is meant separated from other components that naturally accompany it. Typically, a factor is substantially pure when it is at least 50%, by weight, free from proteins, antibodies, and naturally-occurring organic molecules with which it is naturally associated, or in reference to a nucleic acid molecule, is free from the nucleic acid sequences that naturally flank the sequence of the nucleic acid molecule. Desirably, the factor is at least 75%, more desirably, at least 90%, and most desirably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques, such as those described by Ausubel et al. (Current Protocols in Molecular Biology, Wiley Interscience, New York, 2001). The factor is desirably at least 2, 5, or times as pure as the starting material, as measured using polyacrylamide gel electrophoresis, column chromatography, optical density, HPLC analysis, or Western analysis (Ausubel et al., Current Protocols in Molecular Biology, Wiley Interscience, New York, 2001). Desirable methods of purification include immunoprecipitation, column chromatography such as immunoaffinity chromatography and nickel affinity columns, magnetic bead immunoaffinity purification, and panning with a plate-bound antibody.

Other features and advantages of the invention will be apparent from the following Detailed Description, the Drawings, and the Claims.

BRIEF DESCRIPTION OF THE DRAWINGS

In FIG. 3C the morphological changes of antibody SAM-6 induced apoptosis is shown on stomach carcinoma and on pancreas carcinoma cells. Untreated tumor cells grow in homogenous mono-layers. After treatment with antibody SAM-6 the cells become more spindle-shape and flat, more polarized with more pronounced cytoplasmic elongations. A loss of cell contacts and adhesion could be observed already after 48 hours. (Decrease in cell number is caused by apoptosis because cells get in solution as a result of lost adhesion.)

As shown in FIG. 4 initial morphological changes of SAM-6 treated cells after 2 h include the formation of stress fibers (FIG. 4D, E) and a slight reduction of cell-cell contacts. After 24 h drastic morphological changes are observed. Cell-cell contacts are infinitely low (FIG. 4E), cells are either enlarged or condensed the nuclei are swelled (FIG. 4H) and the formation of apoptotic bodies is increased. The most dramatic effects are observed after 48 h. Numerous structural plasma membrane alterations are observed in the apoptotic cells: loss of cellular adhesion, smoothing, shrinkage and out-pouching of membrane segments are recognized as markers associated with cell injury and death. Most important, on the shrunken tumor cells, huge packages of membrane vesicles, apoptotic bodies, are clustered (FIG. 4F). (The formation of smooth-surface apoptotic bodies, as shown at the higher magnification, is due to the fact that in contrast to the in vivo recycling by phagocytic cells, in vitro the membrane vesicles remain sitting on the dead cells.)

FIG. 6 shows the obtained data after 48 h of incubation on gastric cancer cells and on pancreas carcinoma cells, either with antibody SAM-6 or unrelated human control IgM. The gastric carcinoma cell line 23132/87 clearly shows an antibody-induced accumulation of neutral lipids when treated with antibody SAM-6 (FIG. 6A). The cells treated with unrelated human control IgM do not exhibit similar intracellular changes. The same results were observed with the pancreas carcinoma cell line BXPC-3 (FIG. 6B).

FIGS. 7A and D show yellow staining for non-polar, neutral lipids, FIGS. 7B and E red staining for polar lipids, and FIGS. 7C and F an overlay of both. As expected, an intense yellow fluorescence stain for neutral lipids in the SAM-6 treated cells can be seen after 48 h (FIG. 7D). An increase is visible for SAM-6 treated cells stained for polar lipids (FIG. 7E), compared to the control (FIG. 7B), indicating a higher amount of membranes proteins. Since the antibody SAM-6 induces apoptosis, the higher amount of polar lipids is most likely the result of more membranes vesicle formation, namely apoptotic bodies. In the overlay, seen in FIGS. 7C and F, polar lipids are seen in red and neutral lipids are in yellow and some are in orange, as expected. Although the red fluorescence of Nile red is very intense and there might be a possible red spill-over into the yellow-gold fluorescence measurement, a clear distinction can be made between the neutral and polar lipid staining. Taken together these results show, in addition to the Sudan stain, that the SAM-6 antibody induces neutral lipid accumulation in cancer cells.

FIG. 10b shows that analysis of the volume of tumors corresponds with the analysis of tumor weight. The average volume of tumors of SAM-6 treated mice is 126.3 $mm^3$, while average volume of tumors of mice treated with the control antibody is 158.2 $mm^3$.

SEQUENCE LISTING

Figure 1:
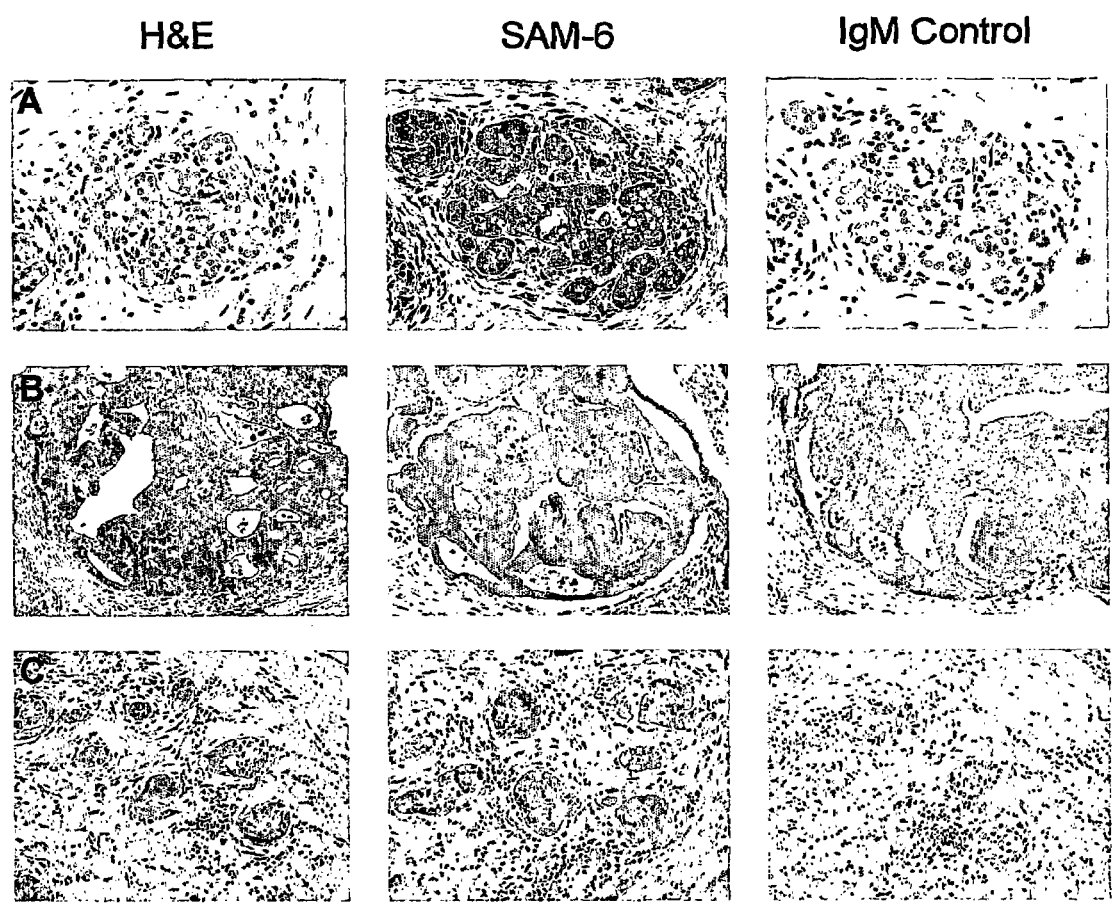
FIG. 1 shows immunohistochemical staining with antibody SAM-6 on tumor tissue. To investigate the specificity of SAM-6 antibody paraffin sections (2 μm) were incubated with antibody SAM-6 at a concentration of 4 μg/ml and unrelated human control with the same iso-type in similar concentration. For morphological analysis one sample was in addition stained with Hematoxilin/Eosin (H&E). Individual images of FIG. 1 show: A, invasive lobular carcinoma of the breast; B, adenocarcinoma of the colon; C, esophageal squamous cell carcinoma (Original magnification ×200). The images in FIG. 1 show that antibody SAM-6 reacts only with tumor cells, whereas the tissues surrounding the malignant areas are not stained.
Figure 2:
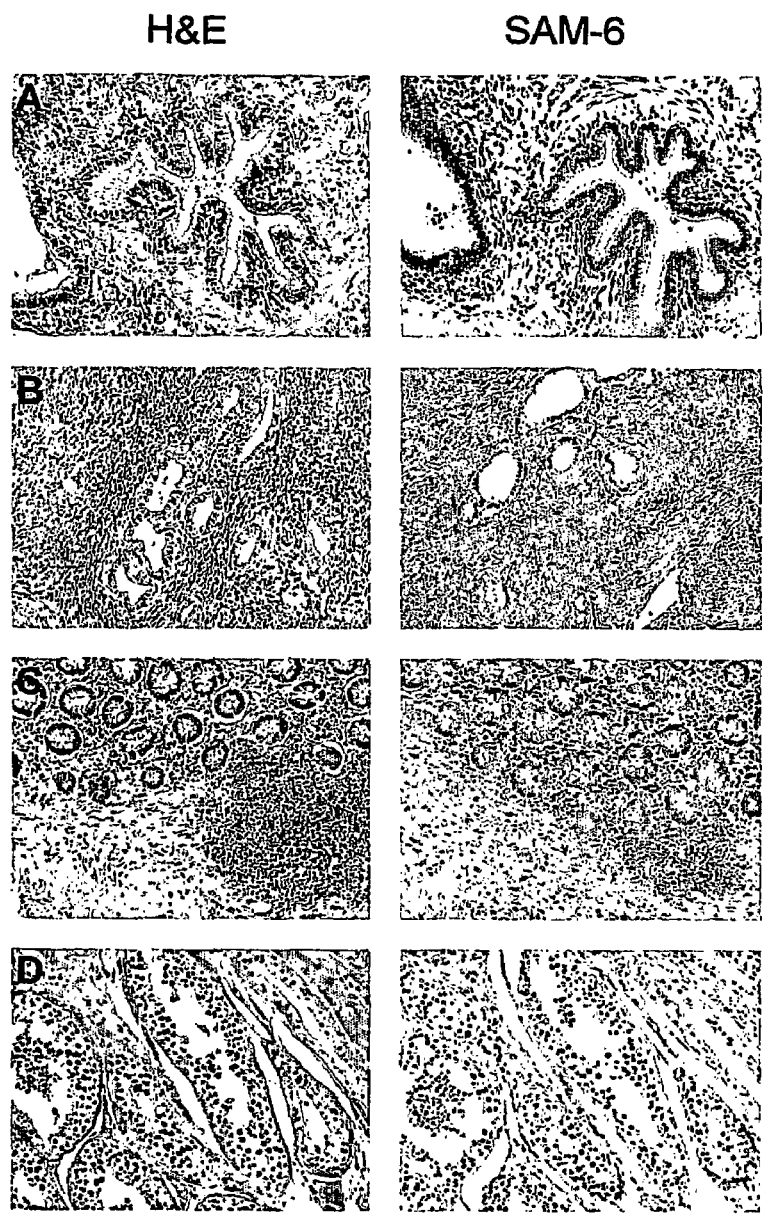
FIG. 2 shows immunohistochemical staining with antibody SAM-6 on normal tissue. Paraffin sections (2 μm) were incubated with antibody SAM-6 at a concentration of 4 μg/ml. For morphological analysis one sample was stained in addition with Hematoxilin/Eosin (H&E). Individual images of FIG. 2 show: A, lung; B, uterus; C, colon; D, testis (Original magnification ×200). Due to the absence of staining with healthy tissue it can be clearly stated that SAM-6 is binding to a receptor specifically expressed on malignant tissue.

The Sequence listing includes sequence protocols of the amino acid sequence (SEQ ID NO:1) (1) and the nucleic acid sequence (SEQ ID NO:2) (2) of the variable region of the light chain ($V_L$) of human monoclonal antibody SAM-6.

Sequence numbers 3 and 4 are the amino acid sequence (SEQ ID NO:3) (3) and the nucleic acid sequence (SEQ ID NO:4) (4) of the variable region of the heavy chain ($V_H$) of human monoclonal anti-body SAM-6.

DETAILED DESCRIPTION

The present invention features polypeptides, such as antibodies, and their use in the treatment and diagnosis of neoplasms. We have characterized a human monoclonal antibody (SAM-6) that specifically recognizes a number of carcinomas. Not only does this monoclonal antibody recognize these neoplasms, but, upon binding to a cell, it can induce apoptosis of neoplastic cells, inhibit their proliferation, or even both. Additionally the antibody (SAM-6) induces the intracellular accumulation of lipids which may cause or support the induction of apoptosis and/or the inhibition of cell-proliferation. Thus, the SAM-6 monoclonal antibody or fragments thereof, that are specific for the antigen recognized by these polypeptides, may be used in a variety of methods for diagnosing and treating a neoplasm.

Antibodies and Polypeptides

Antibodies play an essential role in maintaining the health of an individual. In particular, antibodies are present in serum and bind to and help eliminate diverse pathogens such as bacteria, viruses, and toxins. Antibodies consist of Y-shaped protein structures built from two heavy chains and two light chains. Each chain has a modular construction: each light chain consists of two domains, and each heavy chain has at least four domains. The antigen binding site is fashioned by one domain from the heavy chain ($V_H$ domain) and one domain from the light chain ($V_L$ domain). Indeed, small antigen binding fragments can be prepared by linking these two domains, either associated non-covalently, or covalently via disulphide bonds or a peptide linker. The antigen binding domains are more variable in amino acid sequence than the other domains of the antibody, and are therefore termed variable (V) domains, in contrast to the constant (C) domains. The constant domains of the antibody are responsible for triggering antibody effector mechanisms, such as complement lysis and cell-mediated killing.

Antibodies are made by B-lymphocytes in a process involving gene rearrangement. During the development of these cells, the genes encoding the variable domains are assembled from genetic elements. In the case of the $V_H$ domains there are three elements, the un-rearranged $V_H$ gene, D segment, and $J_H$ segment. In the case of the $V_L$ domains, there are two elements, the un-rearranged $V_L$ (V Lambda or V Kappa) gene and the $J_L$ (J Lambda or J Kappa) segment. Random combination of these gene segments and random combination of the rearranged $V_H$ and $V_L$ domains generate a large repertoire of antibodies, capable of binding to a large diversity of equally diverse antigens.

In general, the presently claimed polypeptide is any agent that binds to BXPC-3, 23132/87, COLO-206F, COLO-699 and LOU-NH91, but does not bind to non-neoplastic cells. The polypeptide may be an antibody, such as a human monoclonal antibody (e.g., SAM-6), or a functional fragment thereof. Overall, the polypeptide of the invention can exclusively bind to both neoplastic tissues and neoplastic cells, but not to non-neoplastic tissue or cells. The polypeptide also may induce apoptosis of a neoplastic cell to which it binds, but not in a non-neoplastic cell, or, alternatively, the polypeptide may inhibit proliferation of the neoplastic cell it binds to, but not in a non-neoplastic cell. Desirably, the polypeptide can simultaneously induce apoptosis and inhibit proliferation of neoplastic cells, but not of non-neoplastic cells. Such a polypeptide is, therefore, useful for the detection, monitoring, prevention, and treatment of cancers in mammals. Exemplary cancers amenable to the methods of the current invention include colorectal cancer, ovarian carcinoma, squamous cell lung carcinoma, small cell lung carcinoma, lobular and ductal mammary carcinomas, melanoma, breast cancer, lung cancer, such as lung adenocarcinomas, gastric cancer, pancreatic cancer, such as pancreatic adenocarcinomas, glioma, sarcomas, gastrointestinal cancer, brain tumor, esophageal cancer, such as esophageal squamous cell carcinomas, stomach cancer, osteosarcoma, fibrosarcomas, urinary bladder cancer, prostate cancer, such as prostate adenocarcinomas, renal cancer, ovarian cancer, testicular cancer, endometrial cancer, cervical cancer, uterine adenocarcinomas, Hodgkin's disease, lymphomas, and leukemias. Such polypeptides are particularly useful for the detection and treatment of adenocarcinoma of the lung, squamous cell lung carcinoma, intestinal type gastric carcinoma, diffuse type gastric carcinoma, adenocarcinoma of the colon, adenocarcinoma of the prostate, squamous cell carcinoma of the esophagus, adenocarcinoma of the esophagus, lobular carcinoma of the breast, ductal carcinoma of the breast, adenocarcinoma of the pancreas, adenocarcinoma of the ovary, or adenocarcinoma of the uterus.

Production

The polypeptides according to the claimed invention can be produced by any method known in the art for small scale, large scale, or commercial production of polypeptides. For example, a monoclonal antibody, such as SAM-6, may be produced by hybridoma cell lines. Such cell lines are typically generated by the fusion of spleen lymphocytes or lymph node lymphocytes derived from patients having a neoplasm, such as stomach carcinoma, colon carcinoma or a pancreatic carcinoma, with a heteromyeloma cell line. Exemplary heteromyeloma cell lines include, for example, HAB-1 (Vollmers et al, Cancer 74:1525-1532, 1994), CB-F7 (Delvig et al., Hum. Antibodies Hybridomas 6:42-46, 1995), K6H6B5 (Delvig et al., Hum. Antibodies Hybridomas 6:42-46, 1995), H7NS.934 (Delvig et al., Hum. Antibodies Hybridomas 6:42-46, 1995), SHM-D33 (Bron et al., Proc. Natl. Acad. Sci. USA 81:3214-3217, 1984), and B6B11 (Borisova et al., Vopr. Virusol. 44:172-174, 1999). The ability to generate human monoclonal antibodies from lymphocytes of cancer patients allows the isolation of antibodies that are generated by an immune response in the cancer patient to the tumor.

Typically, portions of the lymph nodes or spleen are surgically removed from a patient having cancer, such as colon carcinoma or a pancreatic carcinoma. Lymphocytes may be prepared as cell suspensions by mechanical means and subsequently fused at, for example, a 1:2 or 1:3 ratio with a heteromyeloma cell line under conditions that result in cell fusion. For instance, the heteromyeloma cell line HAB-1, which is generated by the fusion of a human lymphocyte with the mouse myeloma NS-0, may be used for this purpose.

Following the fusion of the lymphocytes derived from the cancer patient with the heteromyeloma cell line, an antibody producing hybridoma or trioma is generated. Once constructed, hybridomas are generally stable in growth and antibody production in standard and mass cultures (flasks, miniPerm, fermenters, etc.) for several months. Levels of antibody production typically range between 0.01-0.1 mg/mL in flasks and between 0.1-0.5 mg/mL in miniPerm. Cell fusion may be achieved by any method known in the art, and includes, for example, the use of 40% polyethyleneglycol. Hybridomas may be cultured in media containing HAT (Hypovanthin-aminopterin-thymidin) and after four weeks, supernatants may be screened for antibody production using an ELISA assay. Positive clones may then be tested in be tested in attachment inhibition and binding assays using commercially available tumor cell lines. Positive clones further may be tested using immunoperoxidase staining of tumor and normal tissues. Thus, clones may be selected on the basis of their reactivity with autologous and allogeneic neoplastic cells. The antibody may be purified from mass cultures with use of cation-exchange, hydrophobic interaction, size exclusion, or affinity chromatography, as well as a combination of these methods as described, for example, by Vollmers et al. (Oncology Reports 5:3540, 1998). Following the production of antibodies, additional functional and immunohistochemical tests of the antibodies produced by the trioma may be performed. For example, the antibodies produced by the hybridoma can be tested for their ability to induce apoptosis, inhibit cellular proliferation, or both, relative to untreated control cells. The antibodies can also be tested for their ability to specifically bind the neoplastic cell lines like BXPC-3, 23132/87, COLO-206F, COLO-699 or LOU-NH91, relative to non-neoplastic cells.

Alternatively, the polypeptide, including an antibody, or a fragment thereof, may be produced by the expression of the polypeptide or antibody in a host cell such as *E. coli* or yeast, e.g., *S. cerevisiae*. For example, an antibody of the invention may be identified as follows. A nucleic acid sequence encoding an antibody, or a fragment thereof, may be inserted into filamentous bacteriophage to generate libraries of approximately $10^7$ or more antibodies. Each phage expresses an antibody on its surface that is encoded by the nucleic acid it contains. Antibodies of the invention may thus be screened and detected by functional and histochemical assays as described herein, and such genes may be subsequently selected and expressed in *E. coli*. This system is described, for example, in U.S. Pat. No. 5,876,691.

Antibodies, or functional fragments thereof, may also be generated using, for example, direct synthesis using recombinant methods. These methods are standard in the art. For example, a nucleic acid sequence may be amplified using the polymerase chain reaction (PCR). The PCR technique is known in the art and is described, for example in U.S. Pat. No. 4,683,195. Using standard methods, and as described herein, the sequence of a monoclonal antibody expressed by a hybridoma may be obtained and functional fragments of the antibody may be amplified. For example, whole RNA may be isolated from a hybridoma expressing a tumor-specific monoclonal antibody. cDNA may then be generated from the RNA using reverse transcriptase and the cDNAs which contain the functional fragments of the variable regions of the heavy and light chains may be amplified using PCR. The PCR products may then be purified and cloned into expression vectors, e.g., plasmid or viral vectors. Many standard vectors are available and the selection of the appropriate vector will depend on, for example, the size of the DNA inserted into the vector and the host cell to be transformed with the vector.

Isolation of Amino Acid Variants of a Polypeptide

Amino acid sequence variants of a polypeptide, such as an antibody, e.g., a SAM-6 antibody, can be prepared by introducing appropriate nucleotide changes into the DNA encoding the antibody, or by in vitro synthesis of the desired polypeptide. Such variants include, for example, deletions from, or insertions or substitutions of, residues within the amino acid sequence of the SAM-6 antibody. Any combination of deletion, insertion, and substitution can be made to arrive at the final construct, provided that the final construct possesses the desired characteristics, e.g., the ability to induce apoptosis of a neoplastic cell, but not a non-neoplastic cell, or the ability to inhibit the proliferation of a neoplastic cell, but not a non-neoplastic cell. The amino acid changes also may alter post-translational processes of an antibody, such as changing the number or position of glycosylation sites, altering the membrane anchoring characteristics, or modifying its susceptibility to proteolytic cleavage.

In designing amino acid sequence variants of a polypeptide, such as an antibody, the location of the mutation site and the nature of the mutation will depend on characteristic(s) to be modified. The sites for mutation can be modified individually or in series, e.g., by substituting first with conservative amino acid choices and then with more radical selections depending upon the results achieved, or deleting the target residue.

A useful method for identification of specific residues or regions for mutagenesis in a polypeptide is called "alanine scanning mutagenesis" and is described, for example, by Cunningham and Wells (Science 244:1081-1085, 1989). Here, a residue or group of target residues are identified (e.g., charged residues such as arg, asp, his, lys, and glu) and replaced by a neutral or negatively charged amino acid (most desirably alanine or polyalanine) to affect the interaction of the amino acids with the surrounding aqueous environment in or outside the cell. The domains demonstrating functional sensitivity to the substitutions then are refined by introducing further or other variants at or for the sites of substitution. Thus, while the site for introducing an amino acid sequence variation is predetermined, the nature of the mutation need not be predetermined. For instance, to optimize the performance of a mutation at a given site, alanine scanning or random mutagenesis may be conducted at the target codon or region and the expressed variants are screened for, e.g., the ability to induce apoptosis of a neoplastic cell and not a non-neoplastic cell, or to inhibit the proliferation of a neoplastic cell and not a non-neoplastic cell.

The sites of greatest interest for substitutional mutagenesis include sites identified as affecting the biological activity of a polypeptide. These sites, especially those falling within a sequence of at least three other identically conserved sites, may be substituted in a relatively conservative manner. For instance, ala may be substituted with val, leu, or ile; arg may be substituted with lys, gin, or asn; asn may be substituted with gin, his, lys, or arg; asp may be substituted with glu; cys may be substituted with ser; gln may be substituted with asn; glu may be substituted with asp; gly may be substituted with pro; his may be substituted with asn, gln, lys, or arg; ile may be substituted with leu, val, met, ala, or phe; leu may be substituted with ile, val, met, ala, or phe; lys may be substituted with arg, gln, or asn; met may be substituted with leu, phe, or ile; phe may be substituted with leu, val, ile, or ala; pro may be substituted with gly; ser may be substituted with thr; thr may be substituted with ser; trp may be substituted with tyr; tyr may be substituted with trp, phe, thr, or ser; and val may be substituted with ile, leu, met, or phe.

Conjugation of the Antibody with a Detectable Agent

If desired, the claimed polypeptide such as an antibody (e.g., monoclonal antibody, such as SAM-6), or a fragment thereof, may be linked to a detectable agent to facilitate the purification of the polypeptide as well as the diagnosis, monitoring, or treatment of cancer in a mammal in need thereof. The selection of suitable detectable agent will depend on the intended use of the polypeptide and will be apparent to those of ordinary skill in the art. Detectable agents according to the claimed invention include, for example, protein purification tags, cytotoxins, enzymes, paramagnetic labels, enzyme substrates, co-factors, enzyme inhibitors, dyes, radionuclides, chemiluminescent labels, fluorescent markers, growth inhibitors, and biotin.

A protein purification tag may be conjugated to the polypeptide of the invention, to facilitate isolation of the polypeptide. Examples of tags that can be used include His-tags, HA-tags, FLAG®-tags, and c-Myc tags. An enzymatic or chemical cleavage site may be engineered between the polypeptide and the tag moiety so that the tag can be removed following purification. Suitable toxins include diphtheria toxin, *Pseudomonas* exotoxin A, ricin, and cholera toxin. Examples of suitable enzyme labels include malate hydrogenase, staphylococcal nuclease, delta-5-steroid isomerase, alcohol dehydrogenase, alphaglycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholinesterase. Examples of suitable radioisotopic labels include $^3$H, $^{125}$I, $^{131}$I, $^{32}$P, $^{35}$S, and $^{14}$C. Desirably, the radioisotope will emit in the 10-5,000 kev range, more desirably 100-500 kev. Paramagnetic isotopes may also be conjugated to the polypeptide and used in vivo for the diagnosis and treatment of cancer. The use of such conjugated antibodies may be for in vivo nuclear magnetic resonance imaging. Such a method has previously been described (see, for example, Schaefer et al., JACC 14:472-480, 1989; Shreve et al., Magn. Reson. Med. 3:336-340, 1986; Wolf, Physiol. Chem. Phys. Med. NMR 16:93-95, 1984; Wesbey et al., Physiol. Chem. Phys. Med. NMR 16:145-155, 1984; and Runge et al., Invest. Radiol. 19:408-415, 1984). Alternatively, the radiolabeled antibody may also be used in radioimmunoguided surgery (RIGS), which involves the surgical removal of any tissue the labeled antibody binds to. Thus, the labeled antibody guides the surgeon towards neoplastic tissue by distinguishing it from non-neoplastic tissue. Radiolabels useful for tumor imaging are preferably short-lived radioisotopes. Various radioactive metals with half-lives ranging from 1 hour to 11.4 days are available for conjugation to antibodies, such as scandium-47 (3.4 days), gallium-67 (2.8 days), gallium-68 (68 minutes), technetium-99m (6 hours), indium-111 (3.2 days), and radium-223 (11.4 days), of which gallium-67, technetium-99m, and indium-111 are preferable for gamma camera imaging, gallium-68 is preferable for positron emission tomography, and scandium-47 and radium-223 (and other alpha-emitting radionuclides) are preferable for tumor therapy.

Examples of suitable fluorescent markers include fluorescein, isothiocyalate, rhodamine, phycoerythrin, phycocyanin, allophycocyanin, ophthaldehyde, and fluorescamine. Examples of chemiluminescent markers include a luminal label, isoluminal label, aromatic acridinium ester label, imidazole label, acridinium salt label, oxalate ester label, luciferin label, luciferase label, and aequorin label. Those of ordinary skill in the art would know of other suitable labels, which may be employed in accordance with the present invention. Conjugation of these detectable agents to the claimed polypeptides such as monoclonal antibodies, or fragments thereof, can be accomplished using standard techniques commonly known in the art. Typical anti-body conjugation techniques are described by Kennedy et al. (Clin. Chim. Acta 70, 1-31, 1976) and Schurs et al. (Clin. Chim. Acta 81, 1-40, 1977) and include, for example, the glutaraldehyde method, the periodate method, the dimaleimide method, the m-maleimidobenzyl-N-hydroxy-succinimide ester method. Antibodies may be radiolabeled by any of several techniques known to the art, described, for example, in U.S. Pat. No. 4,444,744. All of these methods are incorporated by reference herein.

In all aspects of the present invention, it is understood that mixtures of different or the same labeled polypeptides specific to different antigens or different epitopes of the same antigen associated with the same or different tumor or tumor cell types may be used. Such a combination may enhance detection, localization and/or therapy in certain cases, and can also increase the range of a broad screen for more than one neoplasm or type of neoplasm.

Polypeptides Conjugated to Anti-Tumor Agents

Although the polypeptide of the invention may induce apoptosis of neoplastic cells, inhibit cellular proliferation of neoplastic cells, or both, the polypeptide may in addition be conjugated to an agent that kills neoplastic cells or that inhibits their proliferation. The targeting ability of the polypeptide, such as an antibody or fragment thereof, results in the delivery of the cytotoxic or anti-proliferative agent to the tumor to enhance the destruction of the tumor. The polypeptide therefore may be used for the treatment and prevention of cancer in a mammal, such as a human patient. The cytotoxic agent linked to the polypeptide may be any agent that destroys or damages a tumor cell or tumor to which the polypeptide has bound. Examples of such agents include chemotherapeutic agents or radioisotopes, enzymes which activates a pro-drug, or a cytokine.

Suitable chemotherapeutic agents are known to those skilled in the art and include, for example, TAXOL™, mithramycin, deoxyco-formycin, mitomycin-C, L-asparaginase, interferons (especially IFN-alpha), etoposide, teniposide, anthracyclines (e.g., daunomycin and doxorubicin), methotrexate, vindesine, neocarzinostatin, cis-platinum, chlorambucil, cytosine arabinoside, 5-fluorouridine, melphalan, ricin, and calicheamicin. The chemotherapeutic agents may be conjugated to the antibody using conventional methods known in the art.

Suitable radioisotopes for use as cytotoxic agents are also known to those skilled in the art and include, for example, $^{131}$I, or an astatine such as $^{211}$At. These isotopes may be attached to the polypeptide, either covalently or non-covalently, using conventional techniques known in the art.

Alternatively, the cytotoxic agent may also be an enzyme, which activates a pro-drug. This allows the conversion of an inactive pro-drug to its active, cytotoxic form at the tumor site and is called "antibody-directed enzyme pro-drug therapy"

(ADEPT). Thus, the polypeptide-enzyme conjugate may be administered to the patient and allowed to localize in the region of the tumor to be treated. The pro-drug is then administered to the patient such that conversion to the cytotoxic drug is localized in the region of the tumor to be treated under the influence of the localized enzyme. An exemplary enzyme is bacterial carboxypeptidase G2 (CPG2) the use of which is described in, for example, WO 88/07378. The polypeptide-enzyme conjugate may, if desired, be modified in accordance with the teaching of WO 89/00427, such as to accelerate its clearance from areas of the body that are not in the vicinity of a neoplasm. The polypeptide-enzyme conjugate may also be used in accordance with WO 89/00427, for example, by providing an additional component, which inactivates the enzyme in areas of the body that are not in the vicinity of the tumor.

As another alternative, the cytotoxic agent conjugated to the claimed polypeptide may also be a cytokine such as interleukin-2 (IL-2), interleukin-4 (IL-4), or tumor necrosis factor alpha (TNF-alpha). The polypeptide targets the cytokine to the tumor so that the cytokine mediates damage to or destruction of the tumor without affecting other tissues. The cytokine may be fused to the polypeptide at the DNA level using conventional recombinant DNA techniques.

In addition, any inhibitor of cell proliferation. e.g., genistein, tamoxifen, or cyclophosphamide, may be conjugated with a polypeptide of the invention.

Dosage

With respect to the therapeutic methods of the invention, it is not intended that the administration of the claimed polypeptide to a patient be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to decrease the number of neoplastic cells by inducing apoptosis of neoplastic cells, by inhibiting proliferation of tumor cells, or both. The compound(s) may be administered to the patient in a single dose or in multiple doses. When multiple doses are administered, the doses may be separated from one another by, for example, one day, two days, one week, two weeks, or one month. For example, the polypeptide (e.g., a monoclonal antibody, such as SAM-6) may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. The precise dose will vary dependent on the polypeptide used, the density, on the tumor surface, of the ligand to which the polypeptide binds, and the rate of clearance of the polypeptide. For example, the dosage of the SAM-6 antibody can be increased if the lower dose does not provide sufficient anti-neoplastic activity. Conversely, the dosage of the SAM-6 antibody can be decreased if the neoplasm is cleared from the patient.

While the attending physician ultimately will decide the appropriate amount and dosage regimen, a therapeutically effective amount of the claimed polypeptide, such as a monoclonal antibody or a fragment thereof, may be, for example, in the range of about 0.1 mg to 50 mg/kg body weight/day or 0.70 mg to 350 mg/kg body weight/week. Desirably a therapeutically effective amount is in the range of about 0.50 mg to 20.0 mg/kg, and more desirably in the range of about 0.50 mg to 15.0 mg/kg for example, about 0.2, 0.3, 0.5, 1.0, 1.5, 2.0, 2.5, 3.0, 3.5, 4.0, 4.5, 5.0, 5.5, 6.0, 7.0, 8.0, 8.5, 9.0, 10.0, 11.0, 12.0, 13.0, 14.0, or 15.0 mg/kg body weight administered daily, every other day, or twice a week.

For example, a suitable dose is an amount of the polypeptide that, when administered as described above, is capable of inducing apoptosis, and is at least 20% above the basal (i.e., untreated) level. In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. According to this invention, the administration of the polypeptide can induce neoplastic cell apoptosis by at least 20%, 40%, 50%, or 75% above that of an untreated control as measured by any standard assay known in the art. More desirably, apoptosis is induced by 80%, 90%, 95%, or even 100% above that of an untreated control. Alternatively, the administration of the polypeptide can inhibit neoplastic cell proliferation by at least 20%, 40%, 50%, or 75% below that of an untreated control as measured by any standard assay known in the art. More desirably, proliferation is inhibited by 80%, 90%, 95%, or even 100% below that of an untreated control. Most desirably, the polypeptide can simultaneously inhibit proliferation and induce apoptosis of neoplastic cells relative to untreated control cells. Such responses can be monitored by any standard technique known in the art. In general, for pharmaceutical compositions, the amount of antibody present in a dose ranges from about 25 µg to 5 mg per kg of host. Suitable dose sizes will vary with the size of the patient, but will typically range from about 0.1 mL to about 5 mL.

Formulation of Pharmaceutical Compositions

The claimed polypeptide may be administered by any suitable means that results in a concentration having anti-neoplastic properties upon reaching the target region. The polypeptide may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. If the neoplastic cells are in direct contact with the blood (e.g., leukemias), or if the tumor is only accessible by the bloodstream then the intravenous (I.V.) route may be used. In cases in which tumors grow in confined spaces such as the pleural cavity or the peritoneal cavity, the polypeptide may be directly administered into the cavity rather than into the blood stream. The formulation and preparation of such compositions are well known to those skilled in the art of pharmaceutical formulation. Formulations can be found in Remington: The Science and Practice of Pharmacy, supra.

Diagnosis and Monitoring Cancer Progression

As discussed above, the present invention is directed to a method for detecting or diagnosing a neoplasm in a mammal, preferably a human patient. Typically, any neoplasm in which administration of the claimed polypeptide causes an induction in apoptosis or a reduction in proliferation are amenable to the methods of this invention.

The claimed polypeptides are particularly useful since they are specific to neoplasms or neoplastic cells, but not normal cells or tissue. Accordingly, this polypeptide can bind to neoplastic cells within the tumor, but not the normal surrounding tissue, thus allowing the detection, the treatment, or both, of a neoplasm in a mammal. For instance, one may use a polypeptide of the invention to determine if a biopsy removed the entire tumor by verifying that no cells bound by the polypeptide remain in the patient or, by verifying that tumor removed from the patient is entirely surrounded by cells that are not bound by the polypeptide.

It is understood that to improve the sensitivity of detection, multiple neoplastic markers may be assayed within a given sample or individual. Thus, polypeptides such as antibodies or functional fragments specific for different antigens may be combined within a single assay, or in multiple assays. Further, multiple primers or probes specific to neoplasms may be used concurrently. The selection of markers may be based on routine experiments to determine combinations that results in optimal sensitivity.

In Vitro Detection of a Neoplasm

In general, the diagnosis of a neoplasm in a mammal involves obtaining a biological sample from the mammal (e.g., human patient), contacting such sample with the polypeptide of the invention (e.g., a monoclonal antibody, such as SAM-6), detecting in the sample the level of reactivity or binding of the polypeptide to neoplastic cells relative to a control sample, which corresponds to non-neoplastic cells derived from healthy tissue from the mammal in which the cancer is being diagnosed or from another patient known not to have neoplasm. Thus, the methods of this invention are particularly useful for the detection of early stage tumors or metastases, which are otherwise undetectable. Accordingly, in addition to diagnosing a neoplasm in a patient, the methods of this invention may also be used to monitor progression of a neoplasm in a mammal. The polypeptide described herein therefore may be used as a marker for the progression of a neoplasm. For this purpose, the assays described below, which are used for the diagnosis of a neoplasm, may be performed over time, and the change in the level of reactive polypeptide(s) evaluated. For example, the assays may be performed every 24-72 hours for a period of 6 months to 1 year, and thereafter performed as needed. In general, a neoplasm is progressing in those patients in whom the level of bound polypeptide detected increases over time. In contrast, the neoplasm is not progressing when the level of bound polypeptide either remains constant or decreases with time. Alternatively, as is noted above, the polypeptide of the invention may also be used to determine the presence of tumor cells in the mammal following tumor resection by surgical intervention to determine whether the tumor has been completely removed from the mammal.

Desirably, the polypeptide is linked to a detectable agent, which facilitates detection, or measurement of polypeptide reactivity. The biological sample is any biological material, which may contain neoplastic cells and include, for example, blood, saliva, tissue, serum, mucus, sputum, urine, or tears. The biological sample may also be a tissue section, which may be fixed tissue, fresh tissue, or frozen tissues. A neoplasm is detected or diagnosed in the mammal from which the sample was obtained if there is an increase in the level of reactivity of the antibody with the biological sample over the control sample. Such increase is at least 10%, 20%, 30%, 40%, 50%, or more than 50% over control levels. The level of binding or reactivity can be determined by any method known in the art and is described in further detail below.

In Vitro Diagnostic Assays

The diagnosis of neoplasms using the claimed polypeptide may be performed by any method known to those of ordinary skill in the art for using a binding agent to detect polypeptide markers in a sample. See, e.g., Harlow and Lane, Antibodies: A Laboratory Manual, Cold Spring Harbor Laboratory, 1988. For example, the polypeptide may be used for enzyme-linked immunosorbent assay (ELISA), Western blotting or in situ detection of tumor cells in a tissue sample. For example, the ELISA assay typically involves the use of the polypeptide, such as an antibody, immobilized on a solid support to bind to the tumor cells in the biological sample. The bound tumor cell may then be detected using a detection reagent that contains a reporter group and that specifically binds to the antibody/tumor cell complex. Such detection reagents include, for example, any binding agent that specifically binds to the antibody, such as an anti-immunoglobulin, protein G, protein A, or a lectin. Alternatively, a competitive assay may be utilized, in which the polypeptide is an antibody and in which the antigens, to which the antibody is specific to is labeled with a reporter group and allowed to bind to the immobilized antibody after incubation of the antibody with the biological sample. The extent to which components of the sample inhibit the binding of the labeled antigens to the antibody is indicative of the reactivity of the sample with the immobilized antibody. Diagnosis of a neoplasm in a patient may also be determined by a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group. For example, to determine the presence or absence of a neoplasm, such as colorectal adenocarcinoma, the signal detected from the reporter group that remains bound to the solid support is generally compared to a signal that corresponds to a pre-determined cut-off value. The cut-off value for the detection of a neoplasm is the average mean signal obtained when the antibody is incubated with samples from patients without a neoplasm.

The method employed for detecting the reporter group depends upon the nature of the reporter group. For radioactive groups, scintillation counting or autoradiographic methods may be used. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a defined period of time), followed by spectroscopic or other analysis of the reaction products.

The polypeptides of the invention may also be employed histologically for in situ detection or quantitative determination of tumor cells, for example, by immunofluorescence or immunoelectron microscopy. In situ detection or determination may be accomplished by removing a tissue specimen from a patient and allowing a labeled antibody to bind to any tumor cell in the specimen. Using such a procedure not only allows the detection of neoplastic cells in a sample, but also allows for the determination of their spatial distribution. As another example, the biological sample can be a smear of biological material containing neoplastic cells on a slide, and the detection of neoplastic cells in the biological material is achieved by examining the smear with a microscope or by fluocytometry.

In Vivo Detection of a Neoplasm

Alternatively, the antibody of the invention may also be used in vivo for detecting and localizing a neoplasm. Such a method may involve injecting a mammal, desirably a human subject, parenterally with a polypeptide of the invention, such as SAM-6, which has been labeled with a detectable agent, and is described, for instance, in U.S. Pat. No. 4,444,744. For example, the polypeptide can be radiolabeled with a pharmacologically inert radioisotope and administered to the patient. The activity of the radioisotope can be detected in the mammal using a photoscanning device, and an increase in activity relative to a control reflects the detection and localization of a neoplasm.

Treatment

In addition to the diagnosis and monitoring of neoplasms in mammals, the present invention also features methods for treating neoplasms in a mammal, desirably a human patient. The method generally involves the administration of a biologically effective amount of the polypeptide of the invention to the patient. The polypeptide is typically administered to the mammal by means of injection using any routes of administration such as by intrathecal, subcutaneous, submucosal, or intracavitary injection as well as for intravenous or intraarterial injection. Thus, the polypeptide may be injected systemically, for example, by the intravenous injection of the polypeptide such as the SAM-6 antibody into the patient's bloodstream or alternatively, the polypeptide can be directly injected at the site of the neoplasm or at a location in proximity to the neoplastic cells.

In general, and as discussed above, binding of the polypeptide of the invention to neoplastic cells results in an induction in apoptosis, a reduction in cellular proliferation, or both relative to the control sample. Alternatively, the antibodies may also activate the complement pathway, which ultimately causes holes to be punctured into the cellular membrane, resulting in cell death.

If desired, the polypeptides may also be conjugated to drugs or toxins as described above. Once attached to the cell surface, the conjugate may be engulfed into the cell cytoplasm where cell enzymes cleave, and, thus, activate or free the drugs or toxins from the conjugate. Once released, the drugs or toxins damage the cell and irreversibly induce cell death. With respect to radiolabeled antibodies, binding to neoplastic cells and the resulting emission of radiation, at a short distance from the cell DNA, produces damage to the latter thus inducing cell death in the next replication round. For example, after a neoplasm has been detected and localized in a subject, a higher dose of labeled antibody, generally from 25 to 250 mCi for $^{131}$I, and preferably from 50 nCi to 150 mCi per dose, based on a 70 kg patient weight, is injected. Injection may be intravenous, intraarterial, intralymphatic, intrathecal, or intracavitary, and may be repeated more than once. It may be advantageous for some therapies to administer multiple, divided doses of radiolabeled polypeptides or polypeptide mixtures, e.g., in the range of 20-120 mCi (70 kg patient), thus providing higher cell-killing doses to the neoplasm without usually effecting a proportional increase in radiation of normal tissues Therapy using labeled polypeptides is advantageously used as a primary therapeutic treatment, but may also be used in combination with other anti-neoplastic therapies, e.g., radiation and chemotherapy, and as an adjunct to surgery. The administration of such conjugated polypeptides is particularly useful in the case where small metastases cannot be surgically removed.

Combination of a Polypeptide with Other Anti-Neoplastic Therapies

Chemotherapeutic agents and/or radiation and/or surgical removal of the neoplasm can optionally be combined with any of the methods of the present invention. Classes of compounds that can be used as the chemotherapeutic agent include: alkylating agents, antimetabolites, natural products and their derivatives, hormones and steroids (including synthetic analogs), and synthetics. Examples of alkylating agents (e.g., nitrogen mustards, ethylenimine derivatives, alkyl sulfonates, nitrosoureas and triazenes) include Uracil mustard, Chlormethine, Cyclophosphamide (CYTOXAN®), Ifosamide, Melphalan, Chlorambucil, Pipobroman, Triethylenemelamine, Triethylenethiophosphoramine, Busulfan, Carmustine, Lomustine, Streptozocin, Dacarbazine, and Temozolomide. Antimetabolites (including folic acid antagonists, pyrimidine analogs, purine analogs and adenosine deaminase inhibitors) may include, for example, Methotrexate, 5-Fluorouracil, Floxuridine, Cytarabine, 6-Mercaptopurine, 6-Thioguanine, Fludarabine phosphate, Pentostatine, and Gemcitabine. Natural products and their derivatives (including vinca alkaloids, antitumor antibiotics, enzymes, lymphokines and epipodophyllotoxins) may also be used and include, for example, Vinblastine, Vincristine, Vindesine, Bleomycin, Dactinomycin, Daunorubicin, Doxorubicin, Epirubicin, Idarubicin, paclitaxel (paclitaxel is commercially available as Taxol, Mithramycin, Deoxyco-formycin, Mitomycin-C, L-Asparaginase, Interferons (especially IFN-alpha), Etoposide, and Teniposide. Hormones and steroids (including synthetic analogs) include, for example, 17-alpha-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, or Zoladex. Exemplary synthetics (including inorganic complexes such as platinum coordination complexes) include Cisplatin, Carboplatin, Hydroxyurea, Amsacrine, Procarbazine, Mitotane, Mitoxantrone, Levamisole, and Hexamethylmelamine.

Methods and dosages for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the disclosure of which is incorporated herein by reference.

The following examples are provided for the purpose of illustrating the invention and should not be construed as limiting.

EXAMPLE 1

Materials and Methods

Cell Culture

In this study the following human cell lines were used: BXPC-3 (pancreatic adenocarcinoma), 23132/87 (gastric adenocarcinoma), COLO-206F (colon carcinoma), COLO-699 (lung adenocarcinoma) and LOU-NH91 (lung squamous cell carcinoma), RPMI-2650 (nasal septum squamous cell carcinoma cell) and HNEpC-c (normal nasal epithelial cells). The cell lines were cultured in RPM1-1640 media (PAA, Vienna, Austria) supplemented with 10% fetal calf serum (FCS), 2 mM glutamine and penicillin/streptomycin (both 1%) and incubated in a humidified, 5% $CO_2$ atmosphere at 37° C. For the assays described, cells were grown to subconfluency, detached with trypsin/EDTA and washed twice with phosphate-buffered saline (PBS) before use.

Producing Hybridomas

We immortalized lymphocytes by fusing them to the HAB-1 heteromyeloma as follows. We washed HAB-1 heteromyeloma cells twice with RPMI 1640 (PAA, Vienna, Austria) without additives and centrifuged the cells for 5 minutes at 1500 rpm. We then thawed frozen lymphocytes obtained from either the spleen or the lymph nodes and we washed these cells twice with RPMI 1640 without additives and centrifuged these cells at 1500 rpm for 5 minutes. Both the HAB-1 and the lymphocyte cell pellets were resuspended in 10 ml RPMI 1640 without additives and were counted in a Neubauer cell counting chamber. We washed the cells again, added the HAB-1 cells and the lymphocytes together in a ratio of 1:2 to 1:3, mixed them, and centrifuged the mixture for 8 minutes at 1500 rpm. We pre-warmed Polyethylene Glycol 1500 (PEG) to 37° C. and carefully let the PEG run drop-wise onto the pellet while slightly rotating the 50 ml tube. Next, we gently resuspended the pellet and rotated the tube for exactly 90 seconds in a 37° C. waterbath. We washed the cells twice with a full 10 ml pipette of RPMI without additives and centrifuged the cells for 5 minutes at 1500 rpm. We added 1 ml of RPMI 1640 with HAT supplement (PAA, Vienna, Austria) and 10% FCS, 1% glutamine, and 1% penicillin/streptomycin ("RPMI 1640 HAT") into each well of a 24-well plate. The cell pellet was dissolved in RPMI 1640 HAT and 0.5 ml of the cells was added to each well of the 24-well plate. We then placed the 24-well plates into a 37° C. incubator and changed the RPMI 1640 HAT medium weekly. After four to six weeks, the cell culture supernatants were screened for antibody production in an enzyme-linked immunosorbent assay (ELISA).

Using this protocol, approximately 80% to 90% of the triomas generated are viable and approximately 50% secrete immunoglobulins. Positive clones were tested immunohistochemically on autologous tumor tissue sections and clones that showed a positive reaction were subsequently re-cloned.

cDNA Synthesis and RT-PCR

To obtain the sequence of the antibody, we isolated whole RNA from the trioma using the RNASE Kit from Qiagen. Total RNA may also be prepared using methods standard in the art, e.g., those described in Krenn et al. (Clin. Exp. Immunol. 115:168-175, 1999). cDNA synthesis from total RNA obtained from hybridoma cell lines SAM-6 was performed with 5 μg total RNA using Gibco BRL (Eggenstein, Germany) M-MLV Reverse Transcriptase according to the manufacturer's instructions. The amplification of $V_H$ and $V_L$ genes was carried out in a 25 μl volume with 1.75 mM $MgCl_2$, 0.4 pM primer, 200 μM of each dNTP, and 1 U Taq polymerase (MBI Fermentas, St. Leon-Rot, Germany). The PCR-products were amplified using the following cycle profiles: 95° C. for 2 min, followed by 35 cycles of 94° C. for 30 sec; 65° C. for 30 sec (for VH3 and VH4 primers), 60° C. for VH1, VH2, VH5, VH6 and 52° C. for $V_L$ primers respectively; a final extension at 72° C. for 4 min.

Sequencing the Antibody

The PCR products were purified using gel electrophoresis through 2% agarose (Roth, Karlsruhe, Germany) followed by gel extraction of the PCR product using a Jetsorb gel extraction kit (Genomed, Bad Oeynhausen, Germany). The PCR products were then cloned using the pCR-Script Amp SK+ cloning kit (Stratagene, Heidelberg, Germany). Ten positive clones were sequenced using the DyeDeoxy termination cycle sequencing kit (Applied BioSystems Inc., Weiterstadt, Germany) and analysed with an ABIPrism373 automated DNA sequencer (both strands were sequenced using T3 and T7 primers). The sequences were analysed using the DNASIS for Windows sequence comparison software and the GenBank and IMGT/V-QUEST databases. The International Immunogenetics ("IMGT") database is coordinated by Marie-Paule Lefranc at the Université Montpellier, Montpellier, France.

Immunohistochemical Staining of Paraffin Sections

Paraffin-embedded human tissues were sectioned (2 μm), the paraffin was removed as follows:

Deparaffinisation:
Xylene 1 5 min
Xylene 2 5 min
100% Ethanol 1 5 min
100% Ethanol 2 5 min
Methanol (70 ml)+$H_2O_2$ (500 μl) 5 min
90% Ethanol 1 3 min
90% Ethanol 2 3 min
80% Ethanol 1 3 min
80% Ethanol 2 3 min
70% Ethanol 1 3 min
70% Ethanol 2 3 min
wash once with Tris/NaCl
cook: 300 ml dest. $H_2O$ in a pressure cooker
    add Citric acid into the inset and cook for 5 min
block 15 min with BSA/PBS, 150 μl per microscope slides
wash once with Tris/NaCl
first antibody: 150 μl per microscope slides, incubate for
    2.5 h in a humidified chamber at 37° C.,
wash three times with Tris/NaCl
second antibody: 150 μl per microscope slides, incubate for
    45 min in a humidified chamber at room temperature
    (700 μl PBS+300 μl AB-Plasma+20 μl antibody)
wash three times with Tris/NaCl
put for 10 min in PBS
incubate 10 min with diaminobenzidine (0.05%)-hydrogen
    peroxide (0.02%): 150 μl per microscope slides
wash three times with $H_2O$, then wash once with dest. $H_2O$
put for 5 min into hematoxylin
put 10-15 min under running tap water
wash with dest. $H_2O$
cover with glycerol gelatine Preparation of Tumor Cell Membrane Extracts Isolation of membrane proteins from tumor cells was performed as described using standard methods in the art, as described, for example, in Hensel et al. (Int. J. Cancer 81:229-235, 1999). In particular, confluent tumor cells (BXPC-3 and 23132/87) were washed twice with PBS, harvested with a cell scraper, centrifuged, and resuspended in hypotonic buffer (20 mM HEPES, 3 mM KCl, 3 mM $MgCl_2$) and incubated for 15 minutes on ice. The cells were then sonicated for 5 minutes and the nuclei were pelleted by centrifugation at 10,000×g for 10 min. The supernatant was centrifuged for 40 minutes at 100,000×g in a swing-out rotor to pellet the membranes. After washing the pellet with hypotonic buffer, the pellet was resuspended in membrane lysis buffer (50 mM HEPES pH 7.4, 0.1 mM EDTA, 10% glycerol, and 1% Triton X-100). Complete protease inhibitor (Boehringer, Mannheim, Germany) also was added to all solutions.

Western Blotting

Western blots were preformed using standard techniques as described, for example, in Hensel et al. (Int. J. Cancer 81:229-235, 1999). In short, blotted nitrocellulose membranes were blocked with PBS containing 3% low fat milk powder, followed by incubation for 1 hour with 2040 μg of SAM-6 human IgM antibodies or unrelated human control IgM (ChromPure IgM, Dianova). The secondary antibody (peroxidase-coupled rabbit anti-human IgM antibody 1:1, 000, Dianova) was detected with the SUPERSIGNAL chemiluminescence kit from Pierce (KMF, St. Augustin, Germany).

Ultra-Structural Studies

Adherent growing stomach carcinoma cell line 23132/87 was incubated with 10 μg/ml SAM-6 antibody or unrelated human control IgM for the indicated periods of time. Then the slides were fixed with 2.5% glutaraldehyde (electron microscopy) or 6.25% glutaraldehyde in Soerensen buffer pH 7.4 (for raster electron microscopy) and pre-pared for microscopical analysis. Morphology of cells was investigated with scanning electron microscopy and transmission electron microscopy.

Sudan III Staining

For intracellular lipid staining stomach carcinoma cells 23132/87 were grown on glass slides. Adherent cells were incubated for 48 h with antibody SAM-6 (30 μg/ml). After two washing steps with PBS cells were fixed for 5 min with 60% isopropanol. Before use, a 60% solution of the Sudan III stock (0.5% Sudan III in 100% isopropanol) was matured overnight, filtered and added to the fixed cells. After 15 min cells were washed with distilled H2O, differentiated in 60% isopropanol, washed again and then counterstained for 6 min with Mayers Hemalaun. Finally cells were rinsed with water for 10 min, washed with distilled H2O and mounted with glycerol gelatin.

Nile Red Staining

The neutral lipid staining with the phenoxazine dye Nile red was performed as described before (Greenspan, P., Mayer, E. P., and Fowler, D. Nile Red: A Selective Fluorescent Stain for Intracellular Lipid Droplets. J. Cell Biol. 100, 965-973, 1985). Briefly, stomach carcinoma cells 23132/87 were grown on glass plates and adherent cells were incubated with SAM-6 antibody (30 g/ml) for 48 h. Cells were then fixed with 1.5% glutaraldehyde for 5 min, washed with HEPES buffer and incubated in a 1:200 dilution of Nile Red in HEPES buffer (stock solution 1 mg/ml Nile red in aceton). After an additional washing step with HEPES buffer cell nuclei were stained with DAPI (dilution 1:1000 in water) for 8 min. Cells were then washed again and mounted with Fluoromount-G (SOUTHERN Biotechnology Ass., Inc., USA). Fluorescence analysis was performed with Leica TCS SP2 confocal laser microscope. Polar lipids are stained dark red (543 nm), neutral lipids are stained yellow (488 nm) and cell nuclei appear blue (350 nm).

Detection of oxLDL

LDL (Sigma, Taufkirchen, Germany) was oxidised by incubation with 20 μM $CuSO_4$ for 3 respectively 15 h. The amount of oxidised LDL was determined with the Mercodia Oxidised LDL ELISA (Mercodia, Uppsala, Sweden)

Mercodia Oxidised LDL ELISA is a solid phase two-site enzyme immunoassay. It is based on the direct sandwich technique in which two monoclonal antibodies are directed against separate antigenic determinants on the oxidised apolipoprotein B molecule. During incubation oxidised LDL in the sample reacts with anti-oxidised LDL antibodies bound to microtitration well. After washing, that removes non-reactive plasma components, a peroxidase conjugated anti-human apolipoprotein B antibody recognizes the oxidised LDL bound to the solid phase. After a second incubation and a single washing Stepp that removes unbound enzyme labeled antibody, the bound conjugate is detected by reaction with 3,3',5,5'-Tetramethylbenzidin (TMB). The reaction is stopped by adding acid to give a colorimetric endpoint that is read spectrophotometrically at 450 nm.

Measuring the SAM-6-oxLDL Interaction

Flexible, flat bottom 96-well plates (Becton Dickinson Labware Europe, France) were incubated with the different oxidised LDL over night at 4° C. Then the plates were blocked using RPMI-1640 medium containing 10% FCS for one hour. Subsequently the plates were incubated with 60 μg/ml SAM-6 antibody diluted in PBS for one hour at 37° C. After washing with PBS three times the plates were incubated with HRP-coupled secondary antibody (rabbit anti human IgM, Dako, Hamburg, Germany) diluted 1:1000 in PBS. Then the plates were washed once with PBS and twice with citrat buffer followed by incubation with OPD (DakoCytomation, Glostrup, Denmark) and measurement at 490 nm in an ELISA-reader.

Chromatographic Analysis of Intracellularly Enriched Lipids

BXPC-3 cells were incubated with 30 μg SAM-6 antibody respectively human unrelated control IgM (Chrompure IgM, Dianova, Germany) for 24 h. Then the cells were detached using trypsin/EDTA, followed by two washing Stepps with PBS. The cell pellets were stored at −20° C. until usage. Lipids were extracted from the cell pellets. The extracted lipids were dissolved in 250 μl Chloroform/Methanol (2:1) and 10 respectively 25 μl were spread at the starting point of a thin layer chromatography plate (coated with $SiO_2$, silica gel). At the outer right and left side the markers with different known lipids (cholesterolester, cholesterol, triglycerids, oleic acid, phospatidylethanolamine, phosphatidylcholine, sphingomyeline) were loaded.

For unpolar lipids hexan/ethylacetat/acetic acid (90/10/1) was used as organic solvent, for phospholipids etc. chloroform/methanol/$H_2O$ (70/30/5) was used. The staining was prepared using a, "Kägi-Miescher" aerosloic reagent (anisaldehyde/sulphuric acid solved in acetic acid) followed by heating to 150° C. until the staining was optimal.

Detection of SAM-6 Activity In-Vivo

To determine the effects of antibody SAM-6 on tumor cell growth in vivo, a scid-mouse/human pancreas carcinoma cell system was used. C.B-17/IcrHanHsd-scid mice (Harlan Winkelmann GmbH, Borchen, Germany) (age 6-8 weeks, n=10 per group) were inoculated with $2 \times 10^6$ human pancreas carcinoma cells (cell line BXPC-3) at day 0 subcutaniously, followed by injections of SAM-6 antibody (200 μg) at days 1, 3, 5, 7 and 9 i.p. post carcinoma cell injection. Control mice were injected with unrelated human IgM (Chrompure IgM, Dianova, Hamburg, Germany) in the same concentration. Visible tumor growth was measured macroscopically during the experiment. The experiments were terminated when tumors had reached maximal tolerable size (day 25), whereupon the mice were sacrificed, tumor volume respectively tumor weight was determined.

EXAMPLE 2

Generation of the Cell Line Expressing the SAM-6 Monoclonal Antibody

As described above, we obtained the SAM-6 monoclonal antibody expressing hybridoma (DSM ACC2903, deposited Apr. 3, 2008, DSMZ, Inhoffenstr. 7B D-38124 Braunschweig) by fusing lymphocytes obtained from the spleen or lymph nodes of a cancer patient with the heteromyeloma cell line HAB-1 (faller, et al., Br. J. Cancer 62:595-598, 1990). The lymphoid sources were not pre-selected in terms of the age or sex of the patient. The resultant cell is a type of hybridoma known as a trioma, as it is the fusion of three cells. Like normal B-lymphocytes, this trioma has to ability to produce antibodies. The specificity of the trioma, as it is the fusion of three cells. Like normal B-lymphocytes, this trioma has to ability to produce antibodies. The specificity of the antibody is determined by the specificity of the original lymphocyte from the patient that was used to generate the trioma.

The hybridoma supernatants were screened for antibody production using an ELISA assay. Following ELISA, antibodies were primarily tested immunohistochemically against their autologous tumor for tumor specific reactivity. The SAM-6 antibody was generated from the stomach of a patient with adenocarcinoma.

Figure 8:
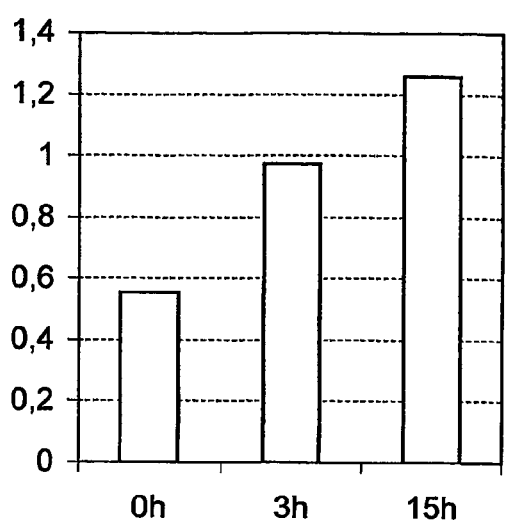
FIG. 8a shows that the amount of oxLDL is increased by incubation of LDL with $CuSO_4$. However, even LDL not incubated with $CuSO_4$ shows a remarkable amount of LDL in its oxidised form (oxLDL).
In FIG. 8b it is documented that oxLDL is a preferred binding-partner of the SAM-6 antibody. The sample incubated with $CuSO_4$ for 15 h binds more SAM-6 antibodies than the sample with an incubation time of 3 h. As an isotype control human unrelated IgM (Chrompure IgM, Dianova) was used.
Figure 8:
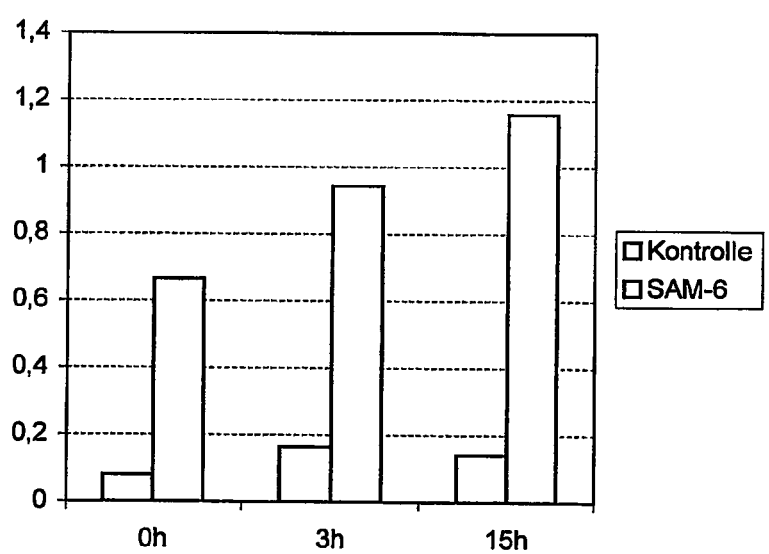
Figure 9A:
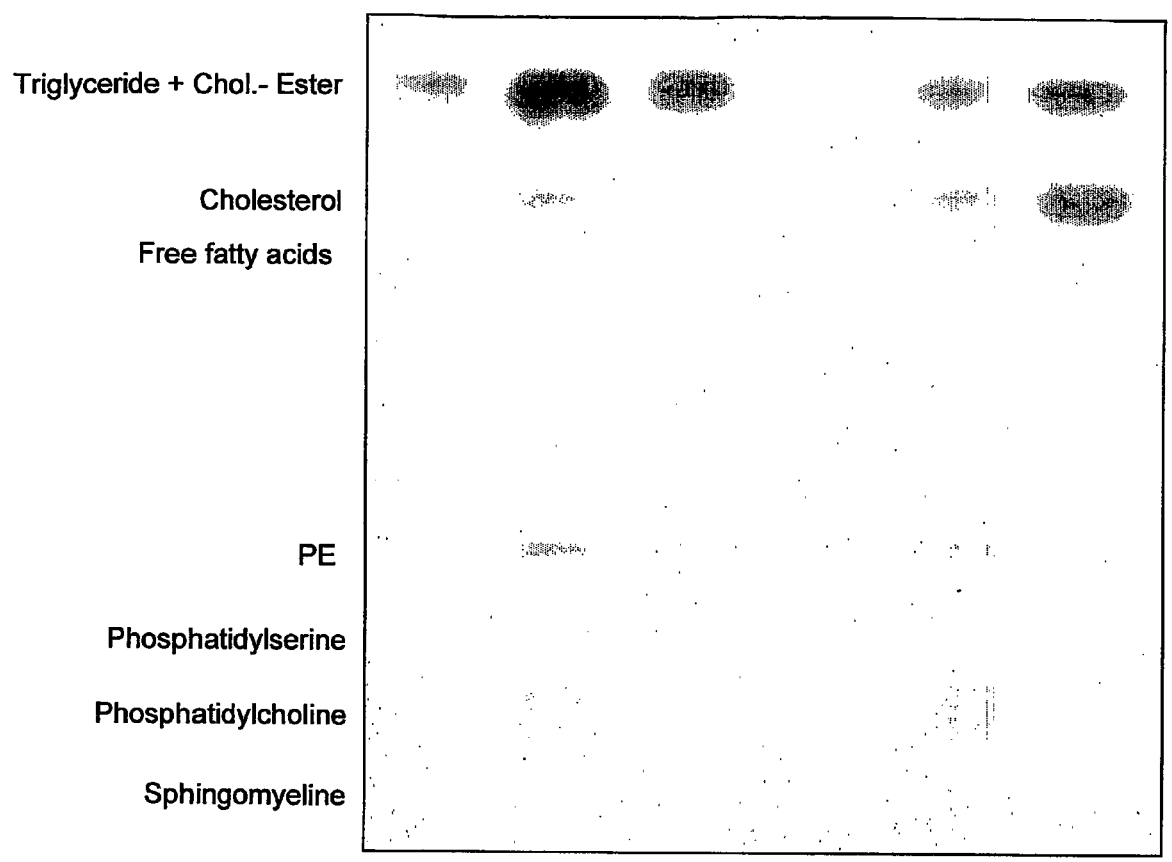
FIG. 9a shows the composition of lipids of cultivated cells analyzed by thin-layer-chromatography. The first lanes on the left and the last lane on the right were loaded with different molecular weight standards. The second and third lane shows the lipid-composition of cells incubate with SAM-6 antibody. Compared to cells incubated with a control antibody those cells treated with SAM-6 antibody were shown to contain more high-molecular-weight lipids like triglyceride and cholesterolester.
Figure 9B:
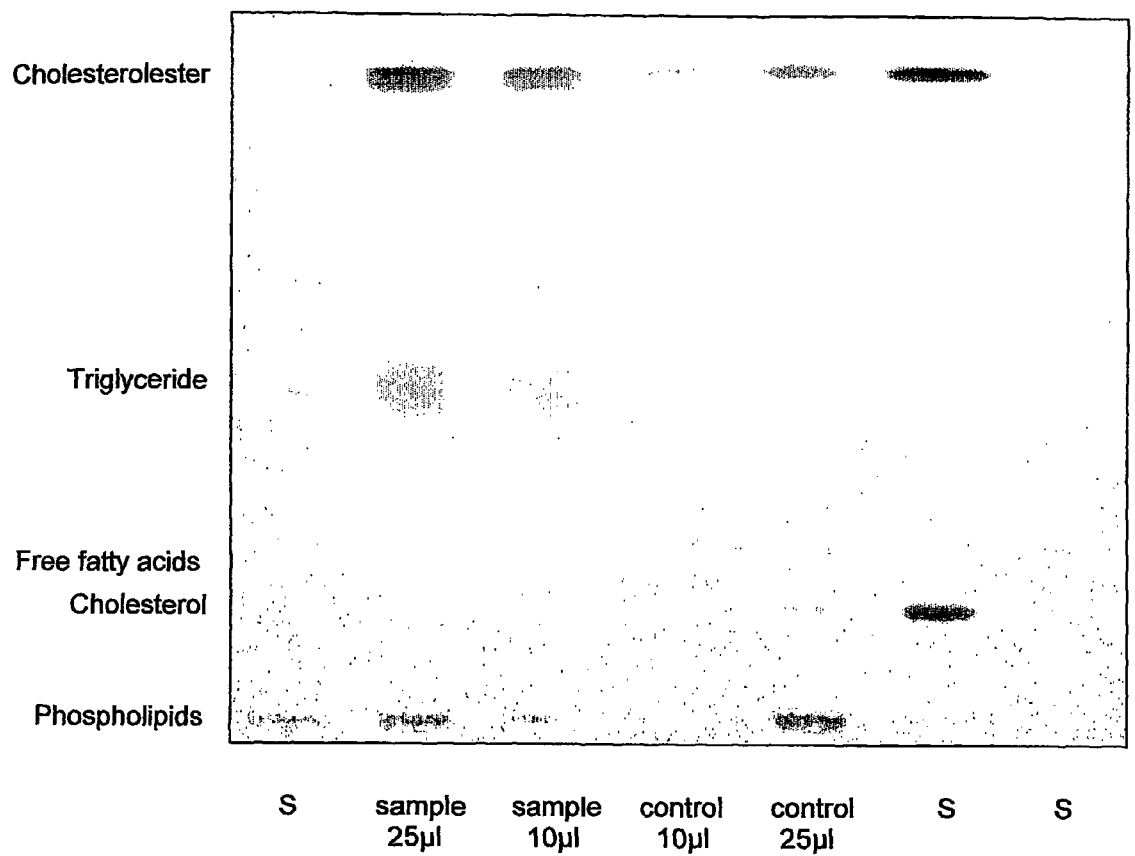
FIG. 9b the high-molecular-weight lipids of the experiment shown in FIG. 9a were further analysed by thin-layer-chromatography. The first lanes on the left and the last lane on the right were loaded with different molecular weight standards. The second and third lane shows the lipid-composition of cells incubate with SAM-6 antibody. Compared to cells incubated with a control antibody those cells treated with SAM-6 antibody contain more Cholesterol and triglycerides.
Figure 10:
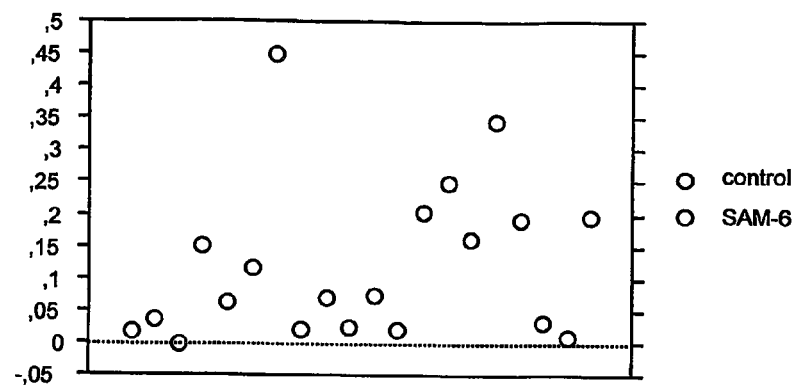
FIG. 10a and 10b show the results of the in-vivo experiments with tumor-inoculated mice which were treated with SAM-6 antibody or a control antibody. According to FIG. 10a the average weight of tumors of SAM-6 treated mice is 96.2 milligrams, while average weight of tumors of mice treated with control antibody is 150.5 milligrams.
Figure 10:
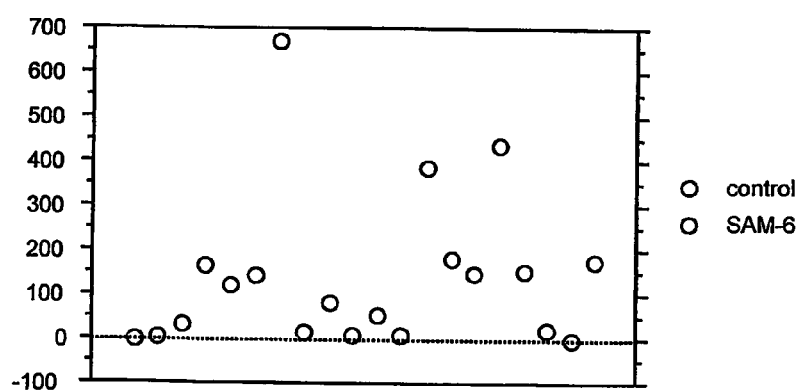
Figure 10A:
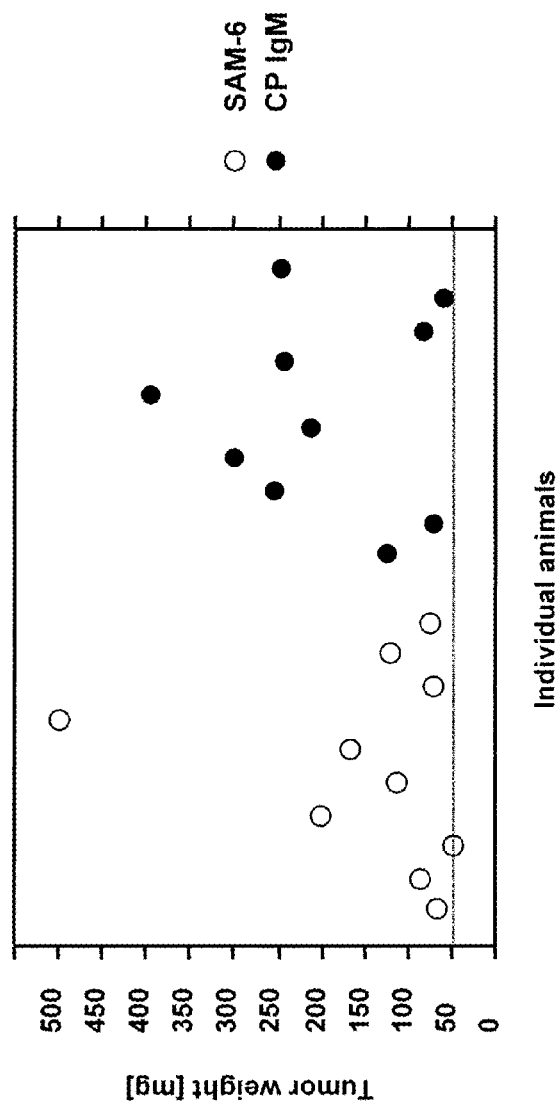
Figure 10B:
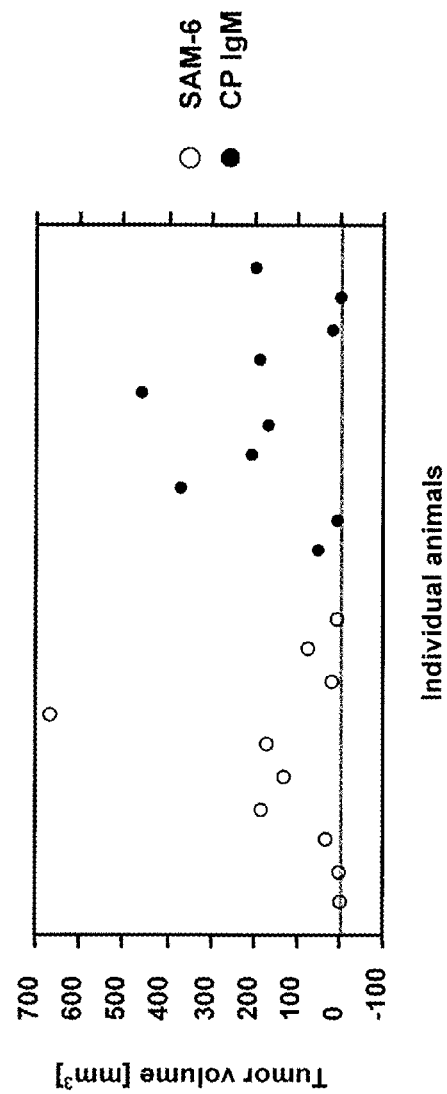
Figure 11:
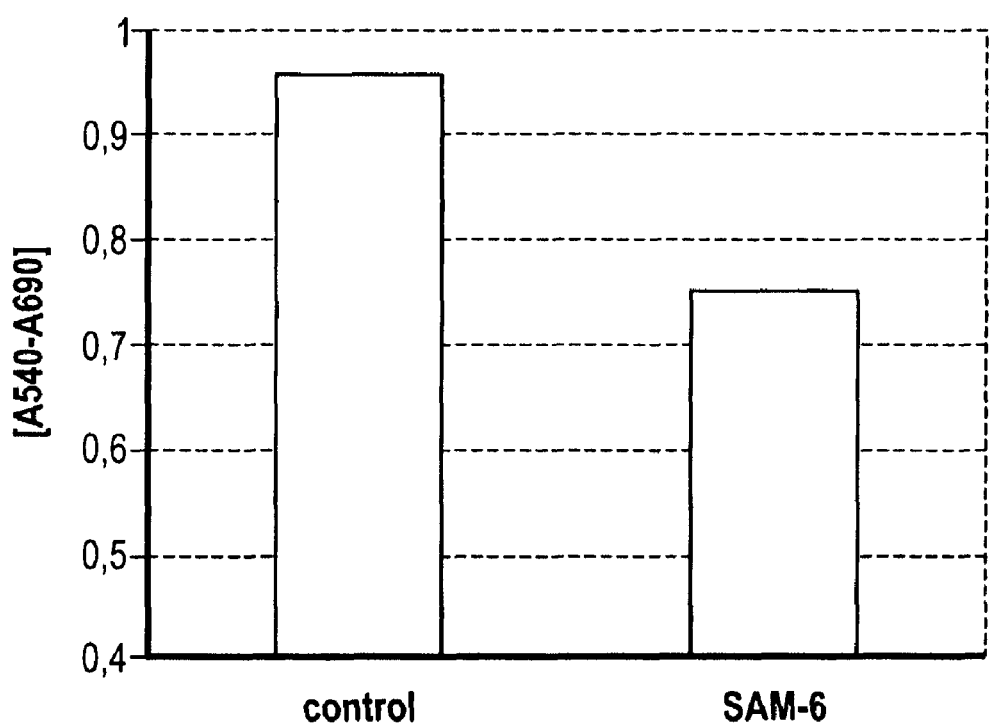
FIG. 11 shows data for the MTT Proliferation Assay; Cell line: 23132/87, Control: RPMI-1640, Antibody: SAM-6 (concentration 4 µg/ml), Time of incubation: 24 h.

The amino acid sequence (SEQ ID NO:1) and the nucleic acid sequence (SEQ ID NO:2) of the variable region of the light chain of human monoclonal antibody SAM-6 are shown in FIGS. 8a and 8b; the amino acid sequence (SEQ ID NO:3) and the nucleic acid sequence (SEQ ID NO:4) of the variable region of the heavy chain of human monoclonal antibody SAM-6 are shown in FIGS. 9a and 9b. In 8b and 9b different complementarity-determining regions (CDRs) are indicated. The complementarity-determining regions (CDRs) of the polypeptides sequence comprises a amino acid sequences that are substantially identical to the amino acid sequences Ser-Gly-Asp-Lys-Leu-Gly-Asp-Lys-Tyr-Ala-Cys (CDR1), Gln-Asp-Ser-Lys-Arg-Pro-Ser (CDR2) and Gln-Ala-TrpAsp-Ser-Ser-Ile-Val-Val (CDR3) of SEQ ID NO 1 of the variable region of the light chain ($V_L$). While the complementarity-determining regions (CDRs) of the polypeptides amino acid sequence comprises a amino acid sequences that are substantially identical to amino acid sequence Ser-Tyr-Ala-Met-His (CDR1), Val-Ile-Ser-Tyr-Asp-Gly-Ser-Asn-Lys-Tyr-Tyr-Ala-Asp-Ser-Val-Lys-Gly (CDR2) and Asp-Arg-Leu-Ala-Val-Ala-Gly-Arg-Pro-Phe-Asp-Tyr (CDR3) of SEQ ID No 3 of the variable region of the heavy chain ($V_H$).

EXAMPLE 3

Immunohistochemical Characterization of an Antibody

To characterize the monoclonal antibody secreted by a hybridoma, we tested the antibody against a panel of normal and tumor tissues using an immunoperoxidase assay as described in the materials and methods. This assay provided us with an overview of which tissues were stained by the antibody and of the distribution of the antigen.

Antibodies that are specific for tumor cells and not for normal tissue were further characterized. First, we tested these antibodies against the same types of tumors from different patients. We then tested these antibodies against tumors of other organs and, finally, against normal tissues. Using these assays, we identified the human SAM-6 monoclonal antibodies. The tumor reactive antibodies generated and described in this study is of the IgM/λ isotype (see Table 1).

TABLE 1

Origin of Monoclonal IgM Antibodies and Clinical Data of Cancer Patients

| Antibody | Organ | Tumor-Type | Tumor-stage | Tumor-grade | Age | Sex | Source Of Lymphocytes | Ig Class |
|---|---|---|---|---|---|---|---|---|
| SAM-6 | Stomach | Adenocarcinoma | T2N2 | G3 | 51 | M | Spleen | IgM/λ |

To investigate the genetic origin of this human monoclonal IgM antibodies the $V_H$ and $V_L$ genes were amplified, cloned and sequenced. The sequences were compared with germ-line sequences in the IMGT/V-QUEST database to identify the most homologous germ-line genes and to detect somatic mutations. The results are represented in Table 2.

TABLE 2

Characterization of Variable Heavy and Light Chain Regions of Monoclonal IgM Antibodies

| | Heavy chain | | | | Light chain | | | |
|---|---|---|---|---|---|---|---|---|
| Antibody | Germ-line Gene | Homology (%) | R/S Frame | R/S CDR | Germ-line gene | Homology (%) | R/S Frame | R/S CDR |
| SAM-6 | IgHV3-30.3 * 01 | 100 | 0/0 | 0/0 | IgLV3-1 * 01 | 99.6 | 1/0 | 0/0 |

The high homology (100%) of the $V_H$ region to the germ-line gene and the low R/S ratio, which is an indicator for affinity maturation of antibodies, indicates that the antibody did not underwent affinity maturation due to antigen contact. The degree of identity of the nucleotide sequence of the $V_L$ segment to the most homologous $V_L$ germ-line gene is again high. The data indicate that the SAM-6 anti-body belongs to the family of naturally occurring, non-affinity matured antibodies.

After initial testing on autologous tumors, the reaction patterns of the antibodies were investigated in greater detail using immunohistochemical staining on a variety of paraffin-embedded carcinomas and normal tissues. The SAM-6 antibody exhibited no binding activity with normal tissues (Table 3).

TABLE 3

Reaction Pattern of the Monoclonal SAM-6 Antibody an Normal Tissue

| Tissue | SAM-6 |
|---|---|
| Esophagus | — |
| Stomach | — |
| Colon | — |
| Pancreas | — |
| Lung | — |
| Breast | — |
| Uterus | — |
| Thyroid gland | — |
| Testis | — |

In contrast, the SAM-6 antibody shows reactivity with different tumor tissues (table 4).

TABLE 4

Reaction Pattern of the Monoclonal IgM SAM-6 Antibody on Tumor Tissues

| Tissue | Carcinoma Type | Pos | Neg |
|---|---|---|---|
| Esophagus | Squamous cell | 3 | 0 |
|  | Adeno (Barrett) | 4 | 0 |
| Stomach | Adeno (diffuse) | 4 | 0 |
|  | Adeno (intestinal) | 3 | 0 |
| Colon | Adeno | 3 | 0 |
| Pancreas | Adeno (ductal) | 3 | 0 |
| Lung | Adeno | 3 | 0 |
|  | Squamous cell | 3 | 1 |
| Breast | Invasive (ductal) | 4 | 0 |
|  | Invasive (lobular) | 4 | 0 |
| Ovary | Adeno | 3 | 0 |
| Uterus | Adeno | 4 | 0 |
| Prostate | Adeno | 5 | 2 |

The positive reaction of antibody SAM-6 was not restricted to adenocarcinoma of the stomach as clear positive reactions were observed, among others, on invasive lobular carcinoma of the breast (FIG. 1A), adenocarcinoma of the colon (FIG. 1B), and squamous cell carcinoma of the esophagus (FIG. 1C). The positive control antibody used in these experiments was a mouse monoclonal antibody against human cytokeratin 5/6 ("CK 5/6;" Dako A/S, Denmark) or a mouse monoclonal antibody against human cytokeratin ("CAM 5.2;" Becton Dickinson, N.J.).

Figure 3:
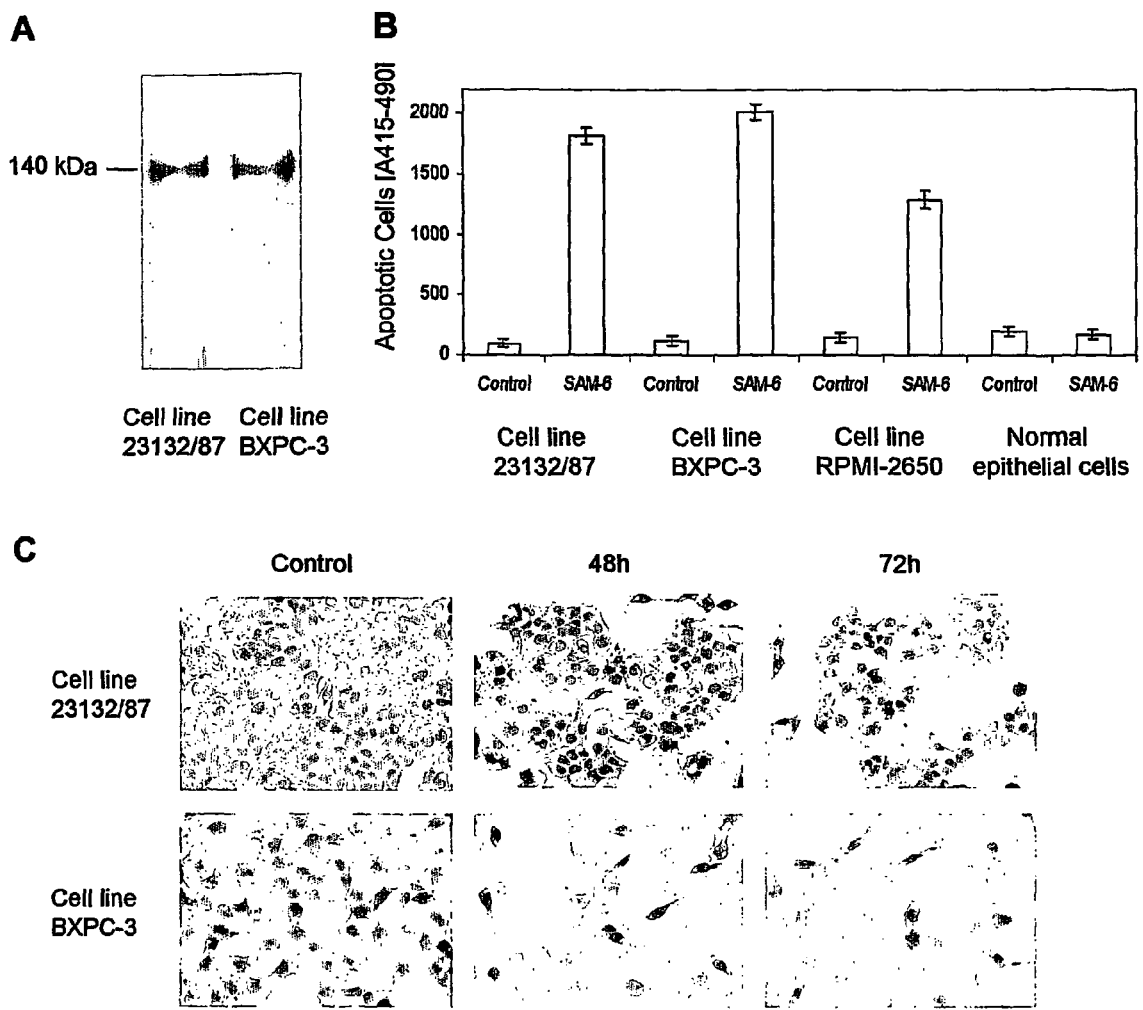
FIG. 3 covers specificity and functional analysis of the SAM-6 anti-body by western blotting, apoptosis assay and morphological analysis. Individual images of FIG. 3 show: A, membrane protein extracts from stomach carcinoma cell line 23132/87 and pancreas carcinoma cell line BXPC-3 were blotted on nitrocellulose and stained with antibody SAM-6. B, Apoptotic activity of antibody SAM-6 was investigated by Cell Death Detection ELISA$^{PLUS}$. Stomach carcinoma cell line 23132/87, pancreas carcinoma cell line BXPC-3, nasal septum squamous cell carcinoma cell line RPMI-2650 and normal nasal epithelial cells (HNEpC-c) were incubated with antibody SAM-6 and isotype control in a concentration of 4 μg/ml for 48 h. Amounts of apoptotic cells were determined photospectrometrically at 415 nm and reference wave length 490 nm. C, antibody induced changes of tumor cell morphology. According to FIG. 3A SAM-6 binds to a membrane molecule with a molecular weight of about 140 kDa. The plot in FIG. 3B illustrates that SAM-6 induces apoptosis of the three tested carcinoma cell types, stomach, pancreas and nasal septum carcinoma cells, but not in normal nasal epithelial cells.
Figure 4:
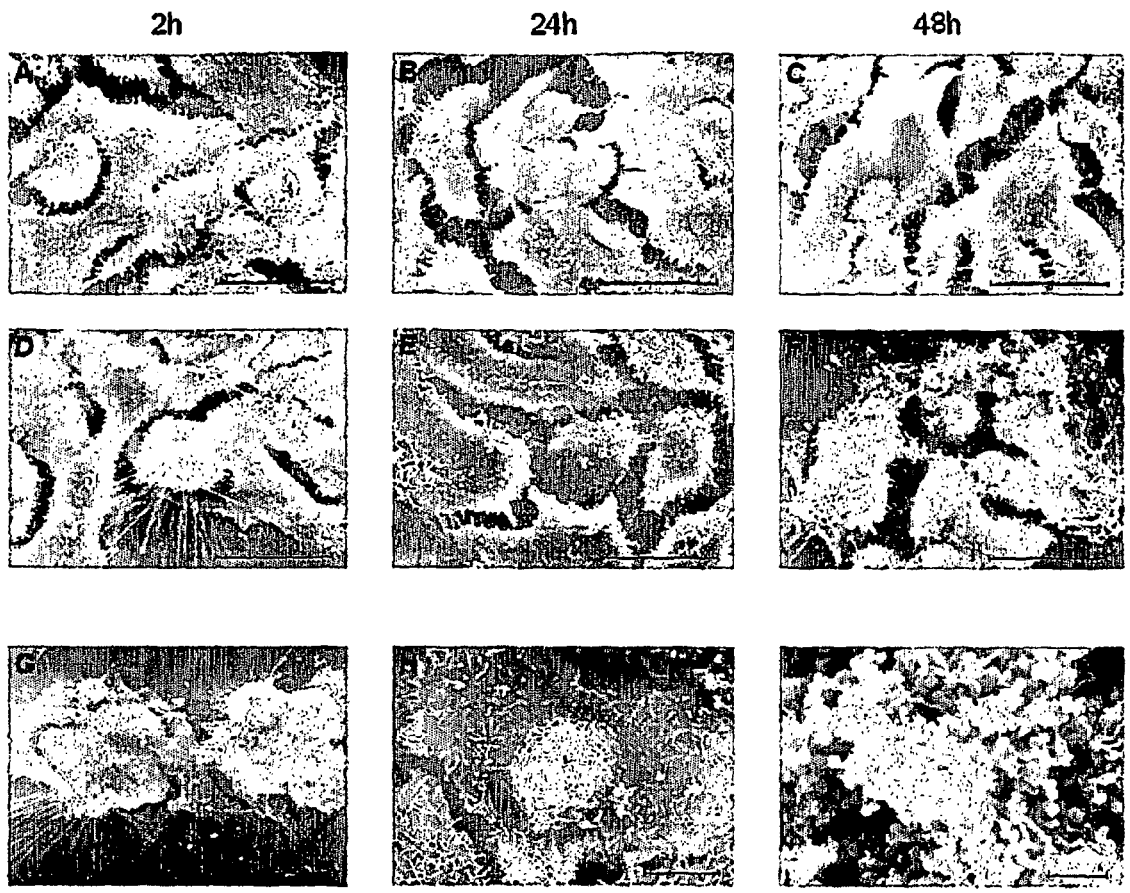
FIG. 4 shows images of SAM-6 antibody induced apoptotic cells by scanning electron microscopy. This technique allows to study morphological and extra-cellular apoptotic effects of cells. For the experiment shown stomach carcinoma cell line 23132/87 was incubated with antibody SAM-6 or isotype control at a concentration of 10 μm/ml for the indicated periods of time. Samples were proceeded for scanning electron microscopy and analyzed by ZEISS DSM 962 at different time points. Individual images of FIG. 4 show: A, B, C, isotype control antibody. D, E, F, SAM-6 antibody, bar indicates 20 μm. Magnification ×3800, bar indicates 20 μm. G, H, I, magnification of SAM-6 apoptotic effects; G, Stress fibers ×7000, bar indicates 10 μm; H, nucleus swelling, ×20000, bar indicates 2 μm; 1, apoptonic bodies, ×40000, bar indicates μm.
Figure 5:
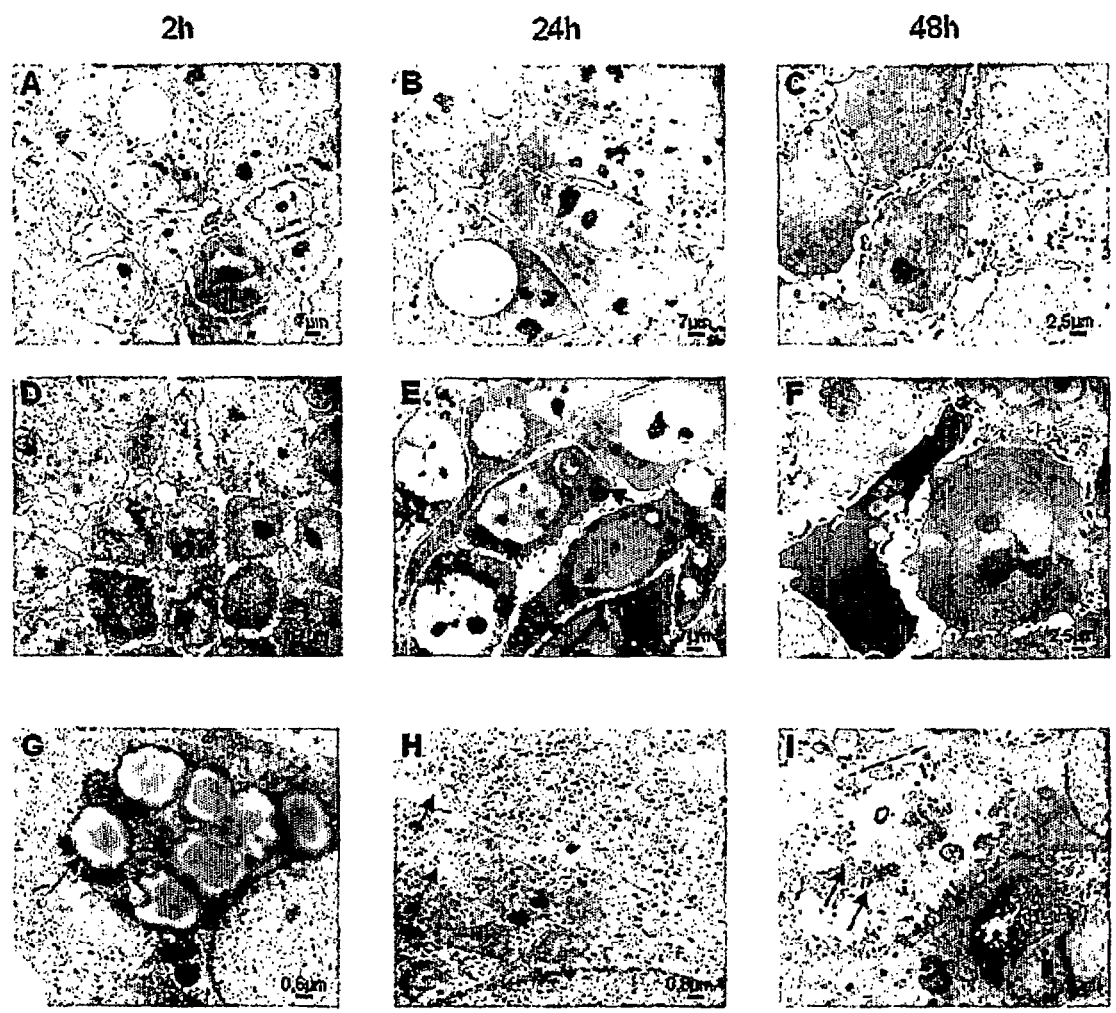
FIG. 5 shows the results of transmission electron microscopy (TEM) experiment. To investigate the intracellular apoptotic effects transmission electron microscopic studies with SAM-6 on stomach carcinoma cells were performed. After 24 h, a drastic change in cell and nuclei shape is observed (FIG. 5E). Cells are enlarged, the cell volume at this stage is not reduced. The cells become spindle-shape, more polarized with more pronounced cytoplasmic elongations. The size of the nuclei is increased, they have a smooth surface and have lost the typical irregular and incised form seen in the control. Most importantly, after 24 h a dramatic accumulation of lipid vesicles in the cytoplasm is clearly visible (FIG. 5E). In almost each of the investigated tumor cells fatty acid depositions can be seen near the nuclei. After 48 h SAM-6 treated cells have reached the final stage of apoptosis (FIG. 5F). The most important structural changes include the disappearance of cell-cell contacts, cell shrinkage, high condensation of nuclei and degradation of plasma and nuclear membranes. The higher magnifications show a cluster of lipid vesicles accumulated in tumor cells (FIG. 5G), nuclear membrane degradation (FIG. 5H) and formation of apoptotic bodies from the cell surface of two tumor cells (FIG. 5I).
Figure 6:
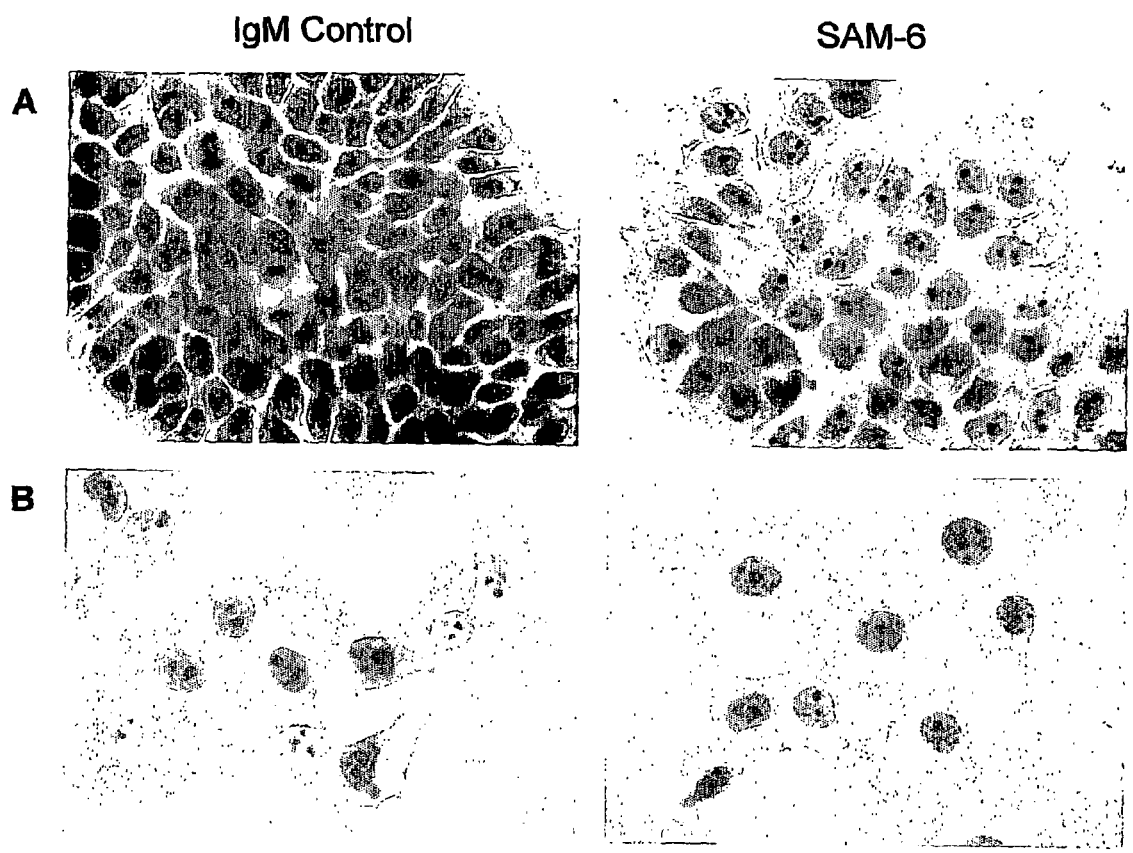
FIG. 6 shows results of Sudan III staining experiments. To examine the antibody-induced lipid accumulation a staining with Sudan III was performed. This dye is specific for the detection of neutral lipids and fatty acids.
Figure 7:
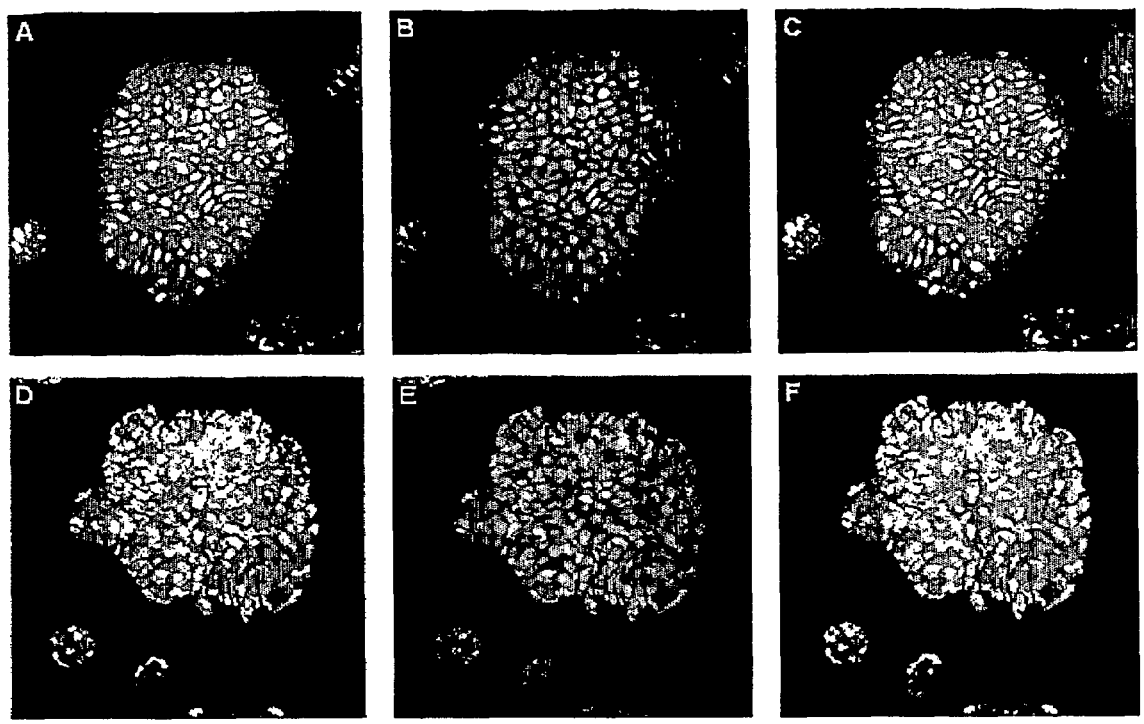
FIG. 7 shows the results of Nile Red staining experiments. Cellular lipids can also be visualized by staining with the fluorescence stain Nile Red. Here, non-polar or neutral lipids stain yellow-gold and polar lipids stain dark red when investigated at specific wavelengths (26, 27). Stomach cancer cells (23132/87) were incubated for 48 h with antibody SAM-6 and investigated for lipid accumulation. Fluorescence was measured at 488 nm for neutral lipids and at 543 nm for polar lipids.

To examine the antigen recognized by the antibody, Western blot analysis was performed with membrane extracts of established carcinoma cell lines. The antibody SAM-6 produced one specific band on stomach carcinoma cell line 23132/87 and pancreas adenocarcinoma cell line BXPC-3. Antibody SAM-6 reacted with membrane proteins of about 140 kDa (FIG. 3A). To rule out non-specific binding of IgM antibodies to membrane extracts, unrelated human control IgM was used as control.

EXAMPLE 4

Determining Whether an Antibody Induces Apoptosis

A number of assays standard in the art may be used to determine if an antibody induces apoptosis of a cell.

For example, we used the CELL DEATH DETECTION ELISA$^{PLUS}$ (Roche, Mannheim, Germany) to analyze the extent to which the SAM-6 antibody induces apoptosis. The cell death detection ELISA is based on a quantitative sandwich-enzyme-immunoassay principle using mouse monoclonal antibodies directed against DNA and histones, respectively. This assay allows the specific determination of mono- and oligo-nucleosomes which are released into the cytoplasm of cells which die from apoptosis.

In particular, $1 \times 10^4$ tumor cells (BXPC-3, 23132/87, RPMI-2650 and HNEpC-c) were plated on 96-well plates and incubated in presence of different concentrations of the human IgM-antibodies for 24 hours at 37° C. and 7% $CO_2$ in an $CO_2$ incubator. Depleted cell culture supernatant with unrelated IgM antibodies served as negative control. After the incubation period, the cells were centrifuged for 10 minutes and the supernatants were removed. The resulting cell pellets were then incubated with lysis-buffer for 30 minutes at room temperature. After centrifugation the supernatants were transferred into a streptavidin-coated microtiter plate (MTP) and immunoreagent (a mixture of 10% Anti-Histone-Biotin, 10% Anti-DNA-peroxidase (Anti-DNA POD) and 80% incubation buffer) added before incubation for 2 hours at room temperature on a MTP shaker at 250 rpm. Following the incubation period, unbound components were removed by a washing step with incubation buffer. POD was determined photometrically with ABTS™ as a substrate (1 ABTS™ (2,2'-Azino-di[3-ethyl-benz-thiazolin-sulfonat) tablet in 5 ml substrate buffer). Antibody-induced apoptosis was measured by determining the color intensity of the green precipitate that it formed as a result of this reaction using an ELISA reader at a wavelength of 405 nm in comparison to ABTS™ solution as a blank (reference wavelength of approximately 490 nm). Based on this color intensity, we calculated the level of the antibody-induced apoptosis. These experiments clearly showed that SAM-6, induces apoptosis in carcinoma cells after 48 hours of incubation (FIG. 3B).

The Y-axis in this figure is the difference between the absorbance at 415 nm and at the 490 nm reference wavelength ($A_{415}$-$A_{490}$) and the negative control is RPMI 1640 medium. The concentration of the SAM-6 antibody was either 4 µg/ml in supernatant.

EXAMPLE 5

Determining Whether an Antibody Inhibits Cell Proliferation

Cell proliferation may be assayed by a number of methods that are standard in the art, for example, by the reduction of tetrazolium salts. The yellow tetrazolium salt 3-(4,5-dimethylthiazol-2-yl)-2,5-diphenyltetrazolium bromide ("MTT") (Sigma, St. Louis, Mo.), is reduced by metabolically active cells, in part by the action of mitochondrial dehydrogenase enzymes to generate reducing equivalents such as NADH and NADPH. The resulting intracellular purple formazan can be solubilized and quantified by spectrophotometric means. The MTT cell proliferation assay measures the rate of cell proliferation and, when metabolic events lead to apoptosis, the reduction in cell viability.

For the MTT assay, we trypsinized cells (23132/87) and resuspended the cells in 10 ml of RPMI-1460 medium contains 10% Fetal Calf Serum (FCS), 1% glutamine, and 1% penicillin/streptomycin (complete medium). The cells were then counted and diluted to $1 \times 10^6$ cells/ml. 50 µl of this suspension were pipetted into wells of a 96-well plate, resulting in approximately $5 \times 10^4$ cells/well. The first row of wells was left empty. We then added 50 µl of the antibody diluted in complete medium to each well. The 96-well plate was then incubated for 24 hours in a 37° C. incubator. After the incubation period, 50 µl MTT solution (5 mg/ml in PBS) were added to each well. The 96-well plate was incubated for 30 minutes at 37° C. and centrifuged for 5 minutes at 800 g. The supernatant was aspirated, 150 µl of dimethylsulphoxide (DMSO) were added to each well, and the cell pellet was resuspended. Absorption was determined at a wavelength of 540 nm and at a reference wavelength of 690 nm in an ELISA reader.

After 24 hours, the SAM-6 antibody inhibited cell proliferation of the tumor cell line, while the controls with depleted cell culture supernatant remained unchanged (see the following figure).

EXAMPLE 6

In Vivo Imaging of a Neoplasm

A patient suspected of having a neoplasm, such as a colorectal carcinoma, may be given a dose of radioiodinated SAM-6 antibody, or another tumor-specific polypeptide, and radiolabeled unspecific anti-body using the methods described herein. Localization of the tumor for imaging may be effected according to the procedure of Goldenberg et al. (N. Engl. J. Med., 298:1384, 1978). By I.V. an infusion of equal volumes of solutions of $^{131}$I-SAM-6 antibody and Tc-99m-labeled unspecific antibody may be administered to a patient. Prior to administration of the reagents I.V., the patient is typically pre-tested for hypersensitivity to the antibody preparation (unlabeled) or to anti-body of the same species as the antibody preparation. To block thyroid uptake of $^{131}$I, Lugol's solution is administered orally, beginning one or more days before injection of the radioiodinated antibody, at a dose of 5 drops twice or three-times daily. Images of various body regions and views may be taken at 4, 8, and 24 hours after injection of the labeled preparations. If present, the neoplasm, e.g., a colorectal carcinoma, is detected by gamma camera imaging with subtraction of the Tc-99m counts from those of $^{131}$I, as described for $^{131}$I-labeled anti-CEA antibody and Tc-99m-labeled human serum albumin by DeLand et al. (Cancer Res. 40:3046, 1980). At 8 hours after injection, imaging is usually clear and improves with time up to the 24 hour scans.

EXAMPLE 7

Treatment of a Neoplasm Using Labeled Antibody Mixtures

A patient diagnosed with a neoplasm, for example, a female patient diagnosed with a breast carcinoma, may be treated with the polypeptides of the invention as follows. Lugol's solution may be administered, e.g., 7 drops 3 times daily, to the patient. Subsequently, a therapeutic dose of $^{131}$I-SAM-6 antibody may be administered to the patient. For example, a $^{131}$I dose of 50 mCi may be given weekly for 3 weeks, and then repeated at intervals adjusted on an individual basis, e.g., every three months, until hematological toxicity interrupts the therapy. The exact treatment regimen is generally determined by the attending physician or person supervising the treatment. The radioiodinated antibodies may be administered as slow I.V. infusions in 50 ml of sterile physiological saline. After the third injection dose, a reduction in the size of the primary tumor and metastases may be noted, particularly after the second therapy cycle, or 10 weeks after onset of therapy.

EXAMPLE 8

Treatment Using Conjugated Antibodies

A patient diagnosed with a neoplasm, for example, a female patient with breast cancer that has metastasized to the chest and lungs, may be treated with solutions of $^{131}$I-SAM-6, $^{10}$B-SAM-6 and a Tc-99m labeled unspecific antibody. An amount of $^{131}$I-labeled SAM-6 anti-body (in 50 ml of sterile physiological saline) sufficient to provide 100 mCi of $^{131}$I activity based on a 70 kg patient weight may be administered to the patient. This dosage is equal to 3.3 mg of an antibody having 40-80 Boron atoms and 8-16 Boron-10 atoms per antibody molecule. The neoplasm is first precisely localized using the procedure of Example 6. In addition, Lugol's solution should be continuously administered to the patient, as in the previous example. A well-collimated beam of thermal neutrons may then be focused on the defined tumor locations. Irradiation with an external neutron beam dose of 400-800 rads, delivered in a period of from 8-20 min, is effected for each tumor locus, and is optionally repeated with administration of the tumor-locating antibody, with or without the radiolabel, at intervals adjusted on an individual basis, but usually not exceeding a total dose of 3200 rads unless simultaneous external irradiation therapy is indicated. If desired, in addition to this therapy, an anti-tumor agent, such as a chemotherapeutic agent, may also be administered to the patient.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

We claim:

1. A purified antibody or functional fragment thereof comprising a light chain ($V_L$) variable region sequence and a heavy chain ($V_H$) variable region sequence, wherein said antibody or functional fragment specifically binds to an epitope of an antigen expressed by at least one of BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196), or LOU-NH91 (DSMZ Accession No. ACC 393) neoplastic cells and binds to apolipoprotein B containing low density lipoproteins (LDL) and apolipoprotein B containing oxidized LDL (oxLDL), wherein SAM-6 antibody comprising the amino acid sequences of SEQ ID NO:1 and SEQ ID NO:3 specifically binds to said epitope of the antigen expressed by at least one of said neoplastic cells, and wherein said heavy chain variable region sequence has CDR sequences identical to CDR1, CDR2 and CDR3 of SEQ ID NO:3.

2. The purified antibody or functional fragment thereof according to claim 1, wherein said functional fragment comprises SEQ NO:1 and SEQ ID NO:3.

3. The purified antibody or functional fragment thereof according to claim 1, wherein said light chain ($V_L$) variable region sequence is at least 80% identical to SEQ ID NO:1, and wherein said heavy chain ($V_H$) variable region sequence is at least 90% identical to SEQ ID NO:3.

4. The purified antibody or functional fragment thereof according to claim 1, comprising the functional fragment thereof.

5. The purified antibody or functional fragment thereof according to claim 4, wherein said functional fragment thereof is selected from the group consisting of $F_v$, Fab, Fab' and $F(ab')_2$.

6. The purified antibody or functional fragment thereof according to claim 1, wherein said light chain variable region sequence has CDR sequences identical to CDR1, CDR2 and CDR3 of SEQ ID NO:1.

7. The purified antibody or functional fragment thereof according to claim 1, wherein the complementary-determining region (CDR) of said light chain ($V_L$) variable region sequence is identical to CDRs [Ser-Gly-Asp-Lys-Leu-Gly-Asp-Lys-Tyr-Ala-Cys (CDR1) and Gln-Asp-Ser-Lys-Arg-Pro-Ser (CDR2) and Gln-Ala-Trp-Asp-Ser-Ser-Ile-Val-Val (CDR3) of SEQ ID NO:1].

8. The purified antibody or functional fragment thereof according to claim 1, wherein said antibody or functional fragment thereof is a monoclonal antibody.

9. The purified antibody or functional fragment thereof according to claim 1, wherein said antibody or functional fragment thereof inhibits cell proliferation of 23132/87 (DSMZ Accession No. ACC 201) cells.

10. The purified antibody or functional fragment thereof according to claim 1, wherein said antibody or functional fragment thereof induces apoptosis of at least one of BXPC-3 (ATCC Accession No. CRL-1687) and 23132/87 (DSMZ Accession No. ACC 201) cells.

11. The purified antibody or functional fragment thereof according to claim 1, wherein the antibody or functional fragment thereof is a monomeric or pentameric form.

12. The purified antibody or functional fragment thereof according to claim 1, wherein said light chain variable region sequence has CDR sequences identical to CDR1, CDR2 and CDR3 of SEQ ID NO:1.

13. The purified antibody or functional fragment thereof according to claim 1, wherein said tight chain ($V_L$) variable region sequence is at least 80% identical to SEQ ID NO:1, or wherein said heavy chain ($V_H$) variable region sequence is at least 90% identical to SEQ ID NO:3.

14. A purified antibody or functional fragment thereof, comprising SEQ ID NO:1 and SEQ ID NO:3.

15. A purified polypeptide comprising a heavy chain ($V_H$) variable region sequence, wherein said heavy chain variable region sequence has CDR sequences identical to CDR1, CDR2 and CDR3 of SEQ ID NO:3, wherein said heavy chain ($V_H$) variable region sequence specifically binds to an epitope of an antigen expressed by at least one of BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196), or LOU-NH91 (DSMZ Accession No. ACC 393) neoplastic cells and binds to apolipoprotein B containing low density lipoproteins (LDL) and apolipoprotein B containing oxidized LDL (ox-LDL), and wherein SAM-6 antibody comprising the amino acid sequences of SEQ ID NO: 1 and SEQ ID NO:3 specifically binds to said epitope of the antigen expressed by at least one of said neoplastic cells.

16. The purified polypeptide according to claim 15, wherein said heavy chain ($V_H$) variable region sequence is at least 95% identical to SEQ ID NO:3.

17. The purified polypeptide according to claim 15, wherein the complementary-determining region (CDR) of said heavy chain ($V_H$) variable region sequence is identical to CDRs [Ser-Tyr-Ala-Met-His (CDR1) and Val-Ile-Ser-Tyr-Asp-Gly-Ser-Asn-Lys-Tyr-Tyr-Ala-Asp-Ser-Val-Lys-Gly (CDR2) and Asp-Arg-Leu-Ala-Val-Ala-Gly-Arg-Pro-Phe-Asp-Tyr (CDR3) SEQ ID NO:3].

18. The purified polypeptide according to claim 15, wherein said heavy chain ($V_H$) variable region sequence is at least 90% identical to SEQ ID NO:3.

19. The purified antibody or functional fragment thereof according to claim 18, wherein said light chain ($V_L$) variable region sequence is at least 95% identical to SEQ ID NO: 1, or wherein said heavy chain variable region sequence is at least 95% identical to SEQ ID NO:3.

20. The purified antibody or functional fragment thereof according to claim 18, wherein said light chain ($V_L$) variable region sequence is at least 90% identical to SEQ ID NO:1, and wherein said heavy chain variable region sequence is at least 90% identical to SEQ ID NO:3.

21. A purified antibody or functional fragment thereof comprising a light chain ($V_L$) variable region sequence and a heavy chain ($V_H$) variable region sequence, wherein said antibody or functional fragment specifically binds to an epitope of an antigen expressed by at least one of BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196), or LOU-NH91 (DSMZ Accession No. ACC 393) neoplastic cells and binds to apolipoprotein B containing low density lipoproteins (LDL) and apolipoprotein B containing oxidized LDL (oxLDL), wherein SAM-6 antibody comprising the amino acid sequences of SEQ ID NO: 1 and SEQ ID NO:3 specifically binds to said epitope of the antigen expressed by at least one of said neoplastic cells, and wherein said light chain ($V_L$) variable region sequence is at least 90% identical to SEQ ID NO: 1, or wherein said heavy chain variable region sequence is at least 90% identical to SEQ ID NO:3.

22. A purified polypeptide comprising a heavy chain ($V_H$) variable region sequence, wherein said heavy chain variable region sequence is at least 90% identical to SEQ ID NO:3, wherein said heavy chain ($V_H$) variable region sequence specifically binds to an epitope of an antigen expressed by at least one of BXPC-3 (ATCC Accession No. CRL-1687), 23132/87 (DSMZ Accession No. ACC 201), COLO-206F (DSMZ Accession No. ACC 21), COLO-699 (DSMZ Accession No. ACC 196), or LOU-NH91 (DSMZ Accession No. ACC 393) neoplastic cells and binds to apolipoprotein B containing low density lipoproteins (LDL) and apolipoprotein B containing oxidized LDL (oxLDL), and wherein SAM-6 antibody comprising the amino acid sequences of SEQ ID NO:1 and SEQ ID NO:3 specifically binds to said epitope of the antigen expressed by at least one of said neoplastic cells.

23. The purified polypeptide according to claim 22, wherein said heavy chain ($V_H$) variable region sequence is at least 95% identical to SEQ ID NO:3.

* * * * *